(12) United States Patent
Ocel et al.

(10) Patent No.: US 7,967,816 B2
(45) Date of Patent: Jun. 28, 2011

(54) FLUID-ASSISTED ELECTROSURGICAL INSTRUMENT WITH SHAPEABLE ELECTRODE

(75) Inventors: Jon Ocel, New Brighton, MN (US); Roderick Briscoe, Rogers, MN (US); David Francischelli, Anoka, MN (US); Scott Jahns, Hudson, WI (US); James R. Keogh, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/056,807

(22) Filed: Jan. 25, 2002

(65) Prior Publication Data

US 2003/0144656 A1 Jul. 31, 2003

(51) Int. Cl.
*A61B 18/18* (2006.01)
(52) U.S. Cl. .................. 606/41; 606/45; 606/49
(58) Field of Classification Search .......... 606/27–52
See application file for complete search history.

(56) References Cited

U.S. PATENT DOCUMENTS

| | | |
|---|---|---|
| 1,127,948 A | 2/1915 | Wappler |
| 1,735,271 A | 11/1929 | Groff |
| 2,004,559 A | 6/1935 | Wappler et al. |
| 3,470,875 A | 10/1969 | Johnson et al. |
| 3,630,207 A | 12/1971 | Kahn et al. |
| 3,736,936 A | 6/1973 | Basiulis et al. |
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,901,242 A | 8/1975 | Storz |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,043,342 A | 8/1977 | Morrison, Jr. |
| 4,061,135 A | 12/1977 | Widran et al. |

(Continued)

FOREIGN PATENT DOCUMENTS

DE 43 13 903 9/1994

(Continued)

OTHER PUBLICATIONS

PCT Search Report mailed on May 15, 2003 (6 pages).

(Continued)

*Primary Examiner* — Roy D Gibson

(57) ABSTRACT

An electrosurgical instrument including an elongated shaft and a non-conductive handle. The shaft defines a proximal section, a distal section, and an internal lumen extending from the proximal section. The distal section forms an electrically conductive tip and defines at least one passage for distributing fluid. Further, the shaft is adapted to be transitionable from a straight state to a first bent state. The shaft is capable of independently maintaining the distinct shapes associated with the straight state and the first bent state. The handle is rigidly coupled to the proximal section of the shaft. With this in mind, an exterior surface of the shaft distal the handle and proximal the distal section is electrically non-conductive. In one preferred embodiment, the shaft is comprised of an elongated electrode body surrounded by an electrical insulator.

17 Claims, 10 Drawing Sheets

U.S. PATENT DOCUMENTS

| | | | |
|---|---|---|---|
| 4,063,560 A | 12/1977 | Thomas et al. | |
| 4,072,152 A | 2/1978 | Linehan | |
| 4,082,096 A | 4/1978 | Benson | |
| 4,207,897 A | 6/1980 | Lloyd et al. | |
| 4,248,224 A | 2/1981 | Jones | |
| 4,275,734 A | 6/1981 | Mitchiner | |
| 4,278,090 A | 7/1981 | van Gerven | |
| 4,312,337 A | 1/1982 | Donohue et al. | |
| 4,326,529 A | 4/1982 | Doss et al. | |
| 4,353,371 A | 10/1982 | Cosman | |
| 4,377,168 A | 3/1983 | Rzasa et al. | |
| 4,492,231 A | 1/1985 | Auth | |
| 4,519,389 A | 5/1985 | Gudkin et al. | |
| 4,590,934 A | 5/1986 | Malis et al. | |
| 4,598,698 A | 7/1986 | Siegmund | |
| 4,601,290 A | 7/1986 | Effron et al. | |
| 4,664,110 A | 5/1987 | Schanzlin | |
| 4,706,667 A | 11/1987 | Roos | |
| 4,732,149 A | 3/1988 | Sutter | |
| 4,736,749 A | 4/1988 | Lundback | |
| 4,779,611 A | 10/1988 | Grooters et al. | |
| 4,802,475 A | 2/1989 | Weshahy | |
| 4,815,470 A | 3/1989 | Curtis et al. | |
| 4,872,346 A | 10/1989 | Kelly-Fry et al. | |
| 4,916,922 A | 4/1990 | Mullens | |
| 4,917,095 A | 4/1990 | Fry et al. | |
| 4,920,982 A | 5/1990 | Goldstein | |
| 4,936,281 A | 6/1990 | Stasz | |
| 4,940,064 A | 7/1990 | Desai | |
| 4,946,460 A | 8/1990 | Merry et al. | |
| 5,009,661 A | 4/1991 | Michelson | |
| 5,013,312 A | 5/1991 | Parins et al. | |
| 5,029,574 A | 7/1991 | Shimamura et al. | |
| 5,033,477 A | 7/1991 | Chin et al. | |
| 5,044,165 A | 9/1991 | Linner et al. | |
| 5,044,947 A | 9/1991 | Sachdeva et al. | |
| 5,071,428 A | 12/1991 | Chin et al. | |
| 5,078,713 A | 1/1992 | Varney | |
| 5,080,102 A | 1/1992 | Dory | |
| 5,080,660 A | 1/1992 | Buelna | |
| 5,083,565 A | 1/1992 | Parins | |
| 5,085,657 A | 2/1992 | Ben-Simhon | |
| 5,087,243 A | 2/1992 | Avitall | |
| 5,100,388 A | 3/1992 | Behl et al. | |
| 5,108,390 A | 4/1992 | Potocky et al. | |
| 5,116,332 A | 5/1992 | Lottick | |
| 5,125,928 A | 6/1992 | Parins et al. | |
| 5,147,355 A | 9/1992 | Friedman et al. | |
| 5,151,102 A | 9/1992 | Kamiyama et al. | |
| 5,156,151 A | 10/1992 | Imran | |
| 5,156,613 A | 10/1992 | Sawyer | |
| 5,167,659 A | 12/1992 | Ohtomo et al. | |
| 5,178,133 A | 1/1993 | Pena | |
| 5,190,541 A | 3/1993 | Abele et al. | |
| 5,207,674 A | 5/1993 | Hamilton | |
| 5,207,691 A | 5/1993 | Nardella | |
| 5,217,460 A | 6/1993 | Knoepfler | |
| 5,217,860 A | 6/1993 | Fahy et al. | |
| 5,222,501 A | 6/1993 | Ideker et al. | |
| 5,224,943 A | 7/1993 | Goddard | |
| 5,228,923 A | 7/1993 | Hed | |
| 5,231,995 A | 8/1993 | Desai | |
| 5,232,516 A | 8/1993 | Hed | |
| 5,242,441 A | 9/1993 | Avitall | |
| 5,242,458 A | 9/1993 | Bendel et al. | |
| 5,250,047 A | 10/1993 | Rydell | |
| 5,250,075 A | 10/1993 | Badie | |
| 5,254,116 A | 10/1993 | Baust et al. | |
| 5,254,130 A | 10/1993 | Poncet et al. | |
| 5,263,493 A | 11/1993 | Avitall | |
| 5,269,291 A | 12/1993 | Carter | |
| 5,269,326 A | 12/1993 | Verrier | |
| 5,269,780 A | 12/1993 | Roos | |
| 5,275,595 A | 1/1994 | Dobak, III | |
| 5,277,201 A | 1/1994 | Stern | |
| 5,281,213 A | 1/1994 | Milder et al. | |
| 5,281,215 A | 1/1994 | Milder | |
| 5,281,216 A | 1/1994 | Klicek | |
| 5,293,869 A | 3/1994 | Edwards et al. | |
| 5,295,484 A | 3/1994 | Marcus et al. | |
| 5,300,087 A * | 4/1994 | Knoepfler | 606/207 |
| 5,306,234 A | 4/1994 | Johnson | |
| 5,309,896 A | 5/1994 | Moll et al. | |
| 5,314,466 A | 5/1994 | Stern | |
| 5,316,000 A | 5/1994 | Chapelon et al. | |
| 5,317,878 A | 6/1994 | Bradshaw et al. | |
| 5,318,525 A | 6/1994 | West et al. | |
| 5,318,589 A | 6/1994 | Lichtman | |
| 5,322,520 A | 6/1994 | Milder | |
| 5,323,781 A | 6/1994 | Ideker et al. | |
| 5,324,255 A | 6/1994 | Passafaro et al. | |
| 5,324,284 A | 6/1994 | Imran | |
| 5,324,286 A | 6/1994 | Fowle | |
| 5,327,905 A | 7/1994 | Avitall | |
| 5,334,181 A | 8/1994 | Rubinsky et al. | |
| 5,334,193 A | 8/1994 | Nardella | |
| 5,336,252 A | 8/1994 | Cohen | |
| 5,348,554 A | 9/1994 | Imran et al. | |
| 5,353,783 A | 10/1994 | Nakao et al. | |
| 5,354,258 A | 10/1994 | Dory | |
| 5,354,297 A | 10/1994 | Avitall | |
| 5,357,956 A | 10/1994 | Nardella | |
| 5,361,752 A | 11/1994 | Moll et al. | |
| 5,364,394 A | 11/1994 | Mehl | |
| 5,383,874 A * | 1/1995 | Jackson et al. | 606/1 |
| 5,385,148 A | 1/1995 | Lesh et al. | |
| 5,395,312 A | 3/1995 | Desai | |
| 5,395,363 A | 3/1995 | Billings et al. | |
| 5,396,887 A | 3/1995 | Imran | |
| 5,397,304 A | 3/1995 | Truckai | |
| 5,397,339 A | 3/1995 | Desai | |
| 5,400,770 A | 3/1995 | Nakao et al. | |
| 5,400,783 A | 3/1995 | Pomeranz et al. | |
| 5,401,272 A | 3/1995 | Perkins | |
| 5,403,309 A | 4/1995 | Coleman et al. | |
| 5,403,311 A | 4/1995 | Abele et al. | |
| 5,403,312 A | 4/1995 | Yates et al. | |
| 5,405,376 A | 4/1995 | Mulier et al. | |
| 5,409,483 A | 4/1995 | Campbell et al. | |
| 5,423,807 A | 6/1995 | Milder | |
| 5,423,811 A | 6/1995 | Imran et al. | |
| 5,427,119 A | 6/1995 | Swartz et al. | |
| 5,429,131 A | 7/1995 | Scheinman et al. | |
| 5,429,636 A | 7/1995 | Shikhman et al. | |
| 5,431,649 A | 7/1995 | Mulier et al. | |
| 5,433,708 A | 7/1995 | Nichols et al. | |
| 5,435,308 A | 7/1995 | Gallup et al. | |
| 5,437,651 A | 8/1995 | Todd et al. | |
| 5,438,302 A | 8/1995 | Goble | |
| 5,441,483 A | 8/1995 | Avitall | |
| 5,441,499 A | 8/1995 | Fritzsch | |
| 5,443,463 A | 8/1995 | Stern et al. | |
| 5,443,470 A | 8/1995 | Stern et al. | |
| 5,445,638 A | 8/1995 | Rydell et al. | |
| 5,449,355 A | 9/1995 | Rhum et al. | |
| 5,450,843 A | 9/1995 | Moll et al. | |
| 5,451,223 A | 9/1995 | Ben-Simhon | |
| 5,452,582 A | 9/1995 | Longsworth | |
| 5,452,733 A | 9/1995 | Sterman et al. | |
| 5,454,370 A | 10/1995 | Avitall | |
| 5,458,596 A | 10/1995 | Lax et al. | |
| 5,458,598 A | 10/1995 | Feinberg et al. | |
| 5,462,545 A | 10/1995 | Wang et al. | |
| 5,465,716 A | 11/1995 | Avitall | |
| 5,465,717 A | 11/1995 | Imran et al. | |
| 5,469,853 A | 11/1995 | Law et al. | |
| 5,472,441 A | 12/1995 | Edwards et al. | |
| 5,472,876 A | 12/1995 | Fahy | |
| 5,478,309 A | 12/1995 | Sweezer et al. | |
| 5,478,330 A | 12/1995 | Imran et al. | |
| 5,480,409 A | 1/1996 | Riza | |
| 5,486,193 A | 1/1996 | Bourne et al. | |
| 5,487,385 A | 1/1996 | Avitall | |
| 5,487,757 A | 1/1996 | Truckai et al. | |
| 5,496,312 A | 3/1996 | Klicek | |
| 5,497,774 A | 3/1996 | Swartz et al. | |
| 5,498,248 A | 3/1996 | Milder | |

| | | | | | | |
|---|---|---|---|---|---|---|
| 5,500,011 A | 3/1996 | Desai | | 5,697,928 A | 12/1997 | Walcott et al. |
| 5,500,012 A | 3/1996 | Brucker et al. | | 5,702,359 A | 12/1997 | Hofmann et al. |
| 5,505,730 A | 4/1996 | Edwards | | 5,702,390 A | 12/1997 | Austin et al. |
| 5,516,505 A | 5/1996 | McDow | | 5,702,438 A | 12/1997 | Avitall |
| 5,520,682 A | 5/1996 | Baust et al. | | 5,709,680 A | 1/1998 | Yates et al. |
| 5,522,788 A | 6/1996 | Kuzmak | | 5,713,942 A | 2/1998 | Stern et al. |
| 5,522,870 A | 6/1996 | Ben-Zion | | 5,716,389 A | 2/1998 | Walinsky et al. |
| 5,531,744 A | 7/1996 | Nardella et al. | | 5,718,241 A | 2/1998 | Ben-Haim et al. |
| 5,536,267 A | 7/1996 | Edwards et al. | | 5,718,701 A | 2/1998 | Shai et al. |
| 5,545,195 A | 8/1996 | Lennox et al. | | 5,718,703 A | 2/1998 | Chin |
| 5,545,200 A | 8/1996 | West et al. | | 5,720,775 A | 2/1998 | Larnard |
| 5,549,636 A | 8/1996 | Li | | 5,722,402 A | 3/1998 | Swanson et al. |
| 5,549,661 A | 8/1996 | Kordis et al. | | 5,722,403 A | 3/1998 | McGee et al. |
| 5,555,883 A | 9/1996 | Avitall | | 5,725,512 A | 3/1998 | Swartz et al. |
| 5,558,671 A | 9/1996 | Yates | | 5,725,524 A | 3/1998 | Mulier et al. |
| 5,560,362 A | 10/1996 | Sliwa, Jr. et al. | | 5,728,143 A | 3/1998 | Gough et al. |
| 5,562,699 A | 10/1996 | Heimberger et al. | | 5,730,074 A | 3/1998 | Peter |
| 5,562,700 A | 10/1996 | Huitema et al. | | 5,730,127 A | 3/1998 | Avitall |
| 5,562,720 A | 10/1996 | Stern et al. | | 5,730,704 A | 3/1998 | Avitall |
| 5,562,721 A | 10/1996 | Marchlinski et al. | | 5,733,280 A | 3/1998 | Avitall |
| 5,564,440 A | 10/1996 | Swartz et al. | | 5,735,280 A | 4/1998 | Sherman et al. |
| 5,569,241 A | 10/1996 | Edwards | | 5,735,290 A | 4/1998 | Sterman et al. |
| 5,569,242 A | 10/1996 | Lax et al. | | 5,735,847 A | 4/1998 | Gough et al. |
| 5,571,088 A | 11/1996 | Lennox et al. | | 5,735,849 A | 4/1998 | Baden et al. |
| 5,571,119 A | 11/1996 | Atala | | 5,738,628 A | 4/1998 | Sierocuk et al. |
| 5,571,215 A | 11/1996 | Sterman et al. | | 5,740,808 A | 4/1998 | Panescu et al. |
| 5,573,532 A | 11/1996 | Chang et al. | | 5,755,664 A | 5/1998 | Rubenstein |
| 5,575,766 A | 11/1996 | Swartz et al. | | 5,755,717 A | 5/1998 | Yates et al. |
| 5,575,788 A | 11/1996 | Baker et al. | | 5,755,760 A | 5/1998 | Maguire et al. |
| 5,575,805 A | 11/1996 | Li | | 5,759,158 A | 6/1998 | Swanson |
| 5,575,810 A | 11/1996 | Swanson et al. | | 5,769,846 A | 6/1998 | Edwards et al. |
| 5,578,007 A | 11/1996 | Imran | | 5,776,130 A | 7/1998 | Buysse et al. |
| 5,582,609 A | 12/1996 | Swanson et al. | | 5,782,826 A | 7/1998 | Swanson |
| 5,584,872 A | 12/1996 | LaFontaine et al. | | 5,782,827 A | 7/1998 | Gough et al. |
| 5,587,723 A | 12/1996 | Otake et al. | | 5,782,828 A | 7/1998 | Chen et al. |
| 5,588,432 A | 12/1996 | Crowley | | 5,785,706 A | 7/1998 | Bednarek |
| 5,590,657 A | 1/1997 | Cain et al. | | H1745 H | 8/1998 | Paraschac |
| 5,591,192 A | 1/1997 | Privitera et al. | | 5,788,636 A | 8/1998 | Curley |
| 5,595,183 A | 1/1997 | Swanson et al. | | 5,792,140 A | 8/1998 | Tu et al. |
| 5,599,348 A * | 2/1997 | Gentelia et al. ................. 606/45 | | 5,796,188 A * | 8/1998 | Bays ............................... 310/50 |
| 5,599,350 A | 2/1997 | Schulze et al. | | 5,797,906 A | 8/1998 | Rhum et al. |
| 5,607,462 A | 3/1997 | Imran | | 5,797,959 A | 8/1998 | Castro et al. |
| 5,609,151 A | 3/1997 | Mulier et al. | | 5,797,960 A | 8/1998 | Stevens et al. |
| 5,611,813 A | 3/1997 | Lichtman | | 5,800,428 A | 9/1998 | Nelson et al. |
| 5,617,854 A | 4/1997 | Munsif | | 5,800,482 A | 9/1998 | Pomeranz et al. |
| 5,620,459 A | 4/1997 | Lichtman | | 5,800,484 A | 9/1998 | Gough et al. |
| 5,630,837 A | 5/1997 | Crowley | | 5,807,393 A | 9/1998 | Williamson, IV et al. |
| 5,632,717 A | 5/1997 | Yoon | | 5,807,395 A | 9/1998 | Mulier et al. |
| 5,637,090 A | 6/1997 | McGee et al. | | 5,810,802 A | 9/1998 | Panescu et al. |
| 5,642,736 A | 7/1997 | Avitall | | 5,810,804 A | 9/1998 | Gough et al. |
| 5,643,197 A | 7/1997 | Brucker et al. | | 5,810,805 A | 9/1998 | Sutcu et al. |
| 5,647,871 A | 7/1997 | Levine et al. | | 5,810,811 A | 9/1998 | Yates et al. |
| 5,649,957 A | 7/1997 | Levin | | 5,814,028 A | 9/1998 | Swartz et al. |
| 5,655,219 A | 8/1997 | Jusa et al. | | 5,817,091 A | 10/1998 | Nardella et al. |
| 5,656,029 A | 8/1997 | Imran et al. | | 5,823,955 A | 10/1998 | Kuck et al. |
| 5,657,755 A | 8/1997 | Desai | | 5,823,956 A | 10/1998 | Roth et al. |
| 5,658,278 A | 8/1997 | Imran et al. | | 5,827,216 A | 10/1998 | Igo et al. |
| 5,671,747 A | 9/1997 | Connor | | 5,827,271 A | 10/1998 | Buysse et al. |
| 5,672,174 A | 9/1997 | Gough et al. | | 5,829,447 A | 11/1998 | Stevens et al. |
| 5,673,695 A | 10/1997 | McGee et al. | | 5,836,947 A | 11/1998 | Fleischman et al. |
| 5,674,220 A | 10/1997 | Fox et al. | | 5,840,030 A | 11/1998 | Ferek-Petric et al. |
| 5,676,662 A | 10/1997 | Fleischhacker et al. | | 5,842,984 A | 12/1998 | Avitall |
| 5,676,692 A | 10/1997 | Sanghvi et al. | | 5,843,075 A | 12/1998 | Taylor |
| 5,676,693 A | 10/1997 | LaFontaine | | 5,843,122 A | 12/1998 | Riza |
| 5,678,550 A | 10/1997 | Bassen et al. | | 5,844,349 A | 12/1998 | Oakley et al. |
| 5,680,860 A | 10/1997 | Imran | | 5,846,187 A | 12/1998 | Wells et al. |
| 5,681,278 A | 10/1997 | Igo et al. | | 5,846,191 A | 12/1998 | Wells et al. |
| 5,681,308 A | 10/1997 | Edwards et al. | | 5,846,238 A | 12/1998 | Jackson et al. |
| 5,683,384 A | 11/1997 | Gough et al. | | 5,849,011 A | 12/1998 | Jones et al. |
| 5,687,723 A | 11/1997 | Avitall | | 5,849,020 A | 12/1998 | Long et al. |
| 5,687,737 A | 11/1997 | Branham et al. | | 5,849,028 A | 12/1998 | Chen |
| 5,688,267 A * | 11/1997 | Panescu et al. ................. 606/41 | | 5,853,411 A | 12/1998 | Whayne et al. |
| 5,688,270 A | 11/1997 | Yates et al. | | 5,855,590 A | 1/1999 | Malecki et al. |
| 5,690,611 A | 11/1997 | Swartz et al. | | 5,855,614 A | 1/1999 | Stevens et al. |
| 5,693,051 A | 12/1997 | Schulze et al. | | 5,860,975 A | 1/1999 | Goble et al. |
| 5,697,536 A | 12/1997 | Eggers et al. | | 5,863,290 A | 1/1999 | Gough et al. |
| 5,697,882 A | 12/1997 | Eggers et al. | | 5,863,291 A | 1/1999 | Schaer |
| 5,697,925 A | 12/1997 | Taylor | | 5,868,737 A | 2/1999 | Taylor et al. |
| 5,697,927 A | 12/1997 | Imran et al. | | 5,871,483 A | 2/1999 | Jackson et al. |

| Patent | Type | Date | Inventor | Patent | Type | Date | Inventor | Class |
|---|---|---|---|---|---|---|---|---|
| 5,871,523 | A | 2/1999 | Fleischman et al. | 6,024,740 | A | 2/2000 | Lesh et al. | |
| 5,871,525 | A | 2/1999 | Edwards et al. | 6,024,741 | A | 2/2000 | Williamson et al. | |
| 5,873,845 | A | 2/1999 | Cline et al. | 6,030,403 | A | 2/2000 | Long et al. | |
| 5,873,896 | A | 2/1999 | Ideker | 6,033,402 | A | 3/2000 | Tu et al. | |
| 5,876,398 | A | 3/1999 | Mulier et al. | 6,036,670 | A | 3/2000 | Wijeratne et al. | |
| 5,876,399 | A | 3/1999 | Chia et al. | 6,039,731 | A | 3/2000 | Taylor et al. | |
| 5,876,400 | A | 3/1999 | Songer | 6,039,733 | A | 3/2000 | Buysse et al. | |
| 5,876,401 | A | 3/1999 | Schulze et al. | 6,039,748 | A | 3/2000 | Savage et al. | |
| 5,879,295 | A | 3/1999 | Li et al. | 6,042,556 | A | 3/2000 | Beach et al. | |
| 5,879,296 | A | 3/1999 | Ockuly et al. | 6,047,218 | A | 4/2000 | Whayne et al. | |
| 5,881,732 | A | 3/1999 | Sung et al. | 6,048,329 | A | 4/2000 | Thompson et al. | |
| 5,882,346 | A | 3/1999 | Pomeranz et al. | 6,050,996 | A | 4/2000 | Schmaltz et al. | |
| 5,883,690 | A | 3/1999 | Meyers et al. | 6,053,172 | A * | 4/2000 | Hovda et al. | 128/898 |
| 5,883,703 | A | 3/1999 | Knirck et al. | 6,056,745 | A | 5/2000 | Panescu | |
| 5,885,278 | A | 3/1999 | Fleischman | 6,063,081 | A | 5/2000 | Mulier et al. | |
| 5,891,135 | A | 4/1999 | Jackson et al. | 6,064,902 | A | 5/2000 | Haissaguerre et al. | |
| 5,891,136 | A | 4/1999 | McGee et al. | 6,068,653 | A | 5/2000 | LaFontaine | |
| 5,891,138 | A | 4/1999 | Tu et al. | 6,071,279 | A | 6/2000 | Whayne et al. | |
| 5,893,848 | A | 4/1999 | Negus et al. | 6,071,281 | A | 6/2000 | Burnside et al. | |
| 5,893,863 | A | 4/1999 | Yoon | 6,083,150 | A | 7/2000 | Aznoian et al. | |
| 5,895,417 | A | 4/1999 | Pomeranz et al. | 6,083,222 | A | 7/2000 | Klein et al. | |
| 5,897,553 | A | 4/1999 | Mulier et al. | 6,088,894 | A | 7/2000 | Oakley et al. | |
| 5,897,554 | A | 4/1999 | Chia et al. | 6,096,037 | A | 8/2000 | Mulier et al. | |
| 5,899,898 | A | 5/1999 | Arless et al. | 6,110,098 | A | 8/2000 | Renirie et al. | |
| 5,899,899 | A | 5/1999 | Arless et al. | 6,113,592 | A | 9/2000 | Taylor | |
| 5,902,289 | A | 5/1999 | Swartz et al. | 6,113,595 | A | 9/2000 | Muntermann | |
| 5,904,711 | A | 5/1999 | Flom et al. | 6,113,598 | A | 9/2000 | Baker | |
| 5,906,580 | A | 5/1999 | Kline-Schoder et al. | 6,117,101 | A | 9/2000 | Diederich et al. | |
| 5,906,587 | A | 5/1999 | Zimmon | 6,117,150 | A | 9/2000 | Pingleton et al. | |
| 5,906,606 | A | 5/1999 | Chee et al. | 6,120,496 | A | 9/2000 | Whayne et al. | |
| 5,908,029 | A | 6/1999 | Knudson et al. | 6,123,702 | A * | 9/2000 | Swanson et al. | 606/34 |
| 5,910,129 | A | 6/1999 | Koblish et al. | 6,123,703 | A | 9/2000 | Tu et al. | |
| 5,913,855 | A | 6/1999 | Gough et al. | 6,126,658 | A | 10/2000 | Baker | |
| 5,916,213 | A | 6/1999 | Haissaguerre et al. | 6,129,662 | A | 10/2000 | Li et al. | |
| 5,916,214 | A | 6/1999 | Cosio et al. | 6,139,545 | A | 10/2000 | Utley et al. | |
| 5,921,924 | A | 7/1999 | Avitall | 6,142,993 | A | 11/2000 | Whayne et al. | |
| 5,921,982 | A | 7/1999 | Lesh et al. | 6,142,994 | A | 11/2000 | Swanson et al. | |
| 5,925,038 | A | 7/1999 | Panescu et al. | 6,152,920 | A | 11/2000 | Thompson et al. | |
| 5,925,042 | A | 7/1999 | Gough et al. | 6,156,009 | A | 12/2000 | Grabek | |
| 5,925,424 | A | 7/1999 | Goswami et al. | 6,156,033 | A | 12/2000 | Tu et al. | |
| 5,927,284 | A | 7/1999 | Borst et al. | 6,161,543 | A * | 12/2000 | Cox et al. | 128/898 |
| 5,928,138 | A | 7/1999 | Knight et al. | 6,162,195 | A | 12/2000 | Igo et al. | |
| 5,928,191 | A | 7/1999 | Houser et al. | 6,162,220 | A | 12/2000 | Nezhat | |
| 5,928,229 | A | 7/1999 | Gough et al. | 6,165,174 | A | 12/2000 | Jacobs et al. | |
| 5,931,810 | A | 8/1999 | Grabek | 6,176,856 | B1 * | 1/2001 | Jandak et al. | 606/29 |
| 5,931,836 | A | 8/1999 | Hatta et al. | 6,185,356 | B1 | 2/2001 | Parker et al. | |
| 5,931,848 | A | 8/1999 | Saadat | 6,193,713 | B1 | 2/2001 | Geistert et al. | |
| 5,935,126 | A | 8/1999 | Riza | 6,203,557 | B1 | 3/2001 | Chin | |
| 5,938,660 | A | 8/1999 | Swartz et al. | 6,206,004 | B1 | 3/2001 | Schmidt et al. | |
| 5,941,251 | A | 8/1999 | Panescu et al. | 6,206,823 | B1 | 3/2001 | Kolata et al. | |
| 5,941,845 | A | 8/1999 | Tu et al. | 6,217,528 | B1 | 4/2001 | Koblish et al. | |
| 5,944,718 | A | 8/1999 | Austin et al. | 6,217,576 | B1 | 4/2001 | Tu et al. | |
| 5,947,938 | A | 9/1999 | Swartz et al. | 6,224,592 | B1 | 5/2001 | Eggers et al. | |
| 5,951,546 | A | 9/1999 | Lorentzen | 6,231,518 | B1 | 5/2001 | Grabek et al. | |
| 5,951,547 | A | 9/1999 | Gough et al. | 6,235,024 | B1 | 5/2001 | Tu | |
| 5,951,552 | A | 9/1999 | Long et al. | 6,237,605 | B1 | 5/2001 | Vaska et al. | |
| 5,954,661 | A | 9/1999 | Greenspon et al. | 6,238,347 | B1 | 5/2001 | Nix et al. | |
| 5,954,665 | A | 9/1999 | Ben-Haim | 6,238,393 | B1 | 5/2001 | Mulier et al. | |
| 5,961,514 | A | 10/1999 | Long et al. | 6,245,061 | B1 | 6/2001 | Panescu et al. | |
| 5,964,755 | A | 10/1999 | Edwards | 6,245,064 | B1 | 6/2001 | Lesh et al. | |
| 5,967,976 | A | 10/1999 | Larsen et al. | 6,245,065 | B1 * | 6/2001 | Panescu et al. | 606/40 |
| 5,971,980 | A | 10/1999 | Sherman | 6,251,092 | B1 | 6/2001 | Qin et al. | |
| 5,971,983 | A | 10/1999 | Lesh | 6,251,128 | B1 | 6/2001 | Knopp et al. | |
| 5,972,013 | A | 10/1999 | Schmidt | 6,264,087 | B1 | 7/2001 | Whitman | |
| 5,972,026 | A | 10/1999 | Laufer et al. | 6,264,670 | B1 | 7/2001 | Chin | |
| 5,980,516 | A | 11/1999 | Mulier et al. | 6,267,761 | B1 | 7/2001 | Ryan | |
| 5,980,517 | A | 11/1999 | Gough | 6,270,471 | B1 | 8/2001 | Hechel et al. | |
| 5,984,281 | A | 11/1999 | Hacker et al. | 6,273,887 | B1 | 8/2001 | Yamauchi et al. | |
| 5,993,447 | A | 11/1999 | Blewett et al. | 6,277,117 | B1 | 8/2001 | Tetzlaff et al. | |
| 5,997,533 | A | 12/1999 | Kuhns | 6,292,678 | B1 | 9/2001 | Hall et al. | |
| 6,007,499 | A | 12/1999 | Martin et al. | 6,293,943 | B1 | 9/2001 | Panescu et al. | |
| 6,010,516 | A | 1/2000 | Hulka | 6,296,619 | B1 | 10/2001 | Brisken et al. | |
| 6,010,531 | A | 1/2000 | Donlon et al. | 6,296,639 | B1 * | 10/2001 | Truckai et al. | 606/41 |
| 6,012,457 | A | 1/2000 | Lesh | 6,296,640 | B1 | 10/2001 | Wampler et al. | |
| 6,013,074 | A | 1/2000 | Taylor | 6,302,880 | B1 | 10/2001 | Schaer | |
| 6,016,809 | A | 1/2000 | Mulier et al. | 6,304,712 | B1 | 10/2001 | Davis | |
| 6,016,811 | A | 1/2000 | Knopp et al. | 6,308,091 | B1 | 10/2001 | Avitall | |
| 6,017,358 | A | 1/2000 | Yoon et al. | 6,311,692 | B1 | 11/2001 | Vaska et al. | |
| 6,023,638 | A | 2/2000 | Swanson | 6,312,383 | B1 | 11/2001 | Lizzi et al. | |

| | | | |
|---|---|---|---|
| 6,314,962 B1 | 11/2001 | Vaska et al. | |
| 6,314,963 B1 | 11/2001 | Vaska et al. | |
| 6,325,797 B1 | 12/2001 | Stewart et al. | |
| 6,328,688 B1 * | 12/2001 | Borst et al. | 600/37 |
| 6,328,736 B1 | 12/2001 | Mulier | |
| 6,332,089 B1 | 12/2001 | Acker et al. | |
| 6,332,881 B1 | 12/2001 | Carner et al. | |
| 6,334,860 B1 | 1/2002 | Dorn | |
| 6,356,790 B1 | 3/2002 | Maguire et al. | |
| 6,358,248 B1 | 3/2002 | Mulier et al. | |
| 6,358,249 B1 | 3/2002 | Chen et al. | |
| 6,361,531 B1 | 3/2002 | Hissong | |
| 6,363,279 B1 | 3/2002 | Ben-Haim et al. | |
| 6,364,876 B1 | 4/2002 | Erb et al. | |
| 6,368,275 B1 | 4/2002 | Sliwa et al. | |
| 6,371,955 B1 | 4/2002 | Fuimaono et al. | |
| 6,383,151 B1 | 5/2002 | Diederich et al. | |
| 6,385,472 B1 | 5/2002 | Hall et al. | |
| 6,391,024 B1 | 5/2002 | Sun et al. | |
| 6,395,038 B1 * | 5/2002 | Schroeppel | 623/23.64 |
| 6,398,792 B1 | 6/2002 | O'Connor | |
| 6,405,078 B1 * | 6/2002 | Moaddeb et al. | 604/21 |
| 6,409,722 B1 | 6/2002 | Hoey et al. | |
| 6,413,254 B1 | 7/2002 | Hissong et al. | |
| 6,419,648 B1 | 7/2002 | Vitek et al. | |
| 6,423,051 B1 | 7/2002 | Kaplan et al. | |
| 6,425,867 B1 | 7/2002 | Vaezy et al. | |
| 6,428,180 B1 | 8/2002 | Karram et al. | |
| 6,430,426 B2 | 8/2002 | Avitall | |
| 6,440,130 B1 | 8/2002 | Mulier et al. | |
| 6,443,952 B1 | 9/2002 | Mulier et al. | |
| 6,443,970 B1 | 9/2002 | Schulze et al. | |
| 6,447,507 B1 | 9/2002 | Bednarek et al. | |
| 6,451,014 B1 * | 9/2002 | Wakikaido et al. | 606/33 |
| 6,461,314 B1 | 10/2002 | Pant et al. | |
| 6,461,956 B1 | 10/2002 | Hsuan et al. | |
| 6,464,700 B1 | 10/2002 | Koblish et al. | |
| 6,471,697 B1 | 10/2002 | Lesh | |
| 6,471,698 B1 | 10/2002 | Edwards et al. | |
| 6,474,340 B1 | 11/2002 | Vaska et al. | |
| 6,475,216 B2 | 11/2002 | Mulier et al. | |
| 6,477,396 B1 | 11/2002 | Mest et al. | |
| 6,484,727 B1 | 11/2002 | Vaska et al. | |
| 6,488,678 B2 | 12/2002 | Sherman | |
| 6,488,680 B1 | 12/2002 | Francischelli et al. | |
| 6,502,575 B1 | 1/2003 | Jacobs et al. | |
| 6,504,985 B2 | 1/2003 | Parker et al. | |
| 6,506,189 B1 | 1/2003 | Rittman, III et al. | |
| 6,506,200 B1 | 1/2003 | Chin | |
| 6,514,250 B1 | 2/2003 | Jahns et al. | |
| 6,517,536 B2 | 2/2003 | Hooven et al. | |
| 6,520,927 B1 * | 2/2003 | Unsworth | 604/19 |
| 6,522,930 B1 | 2/2003 | Schaer et al. | |
| 6,527,767 B2 | 3/2003 | Wang et al. | |
| 6,537,248 B2 | 3/2003 | Mulier et al. | |
| 6,537,272 B2 | 3/2003 | Christopherson et al. | |
| 6,540,740 B2 | 4/2003 | Lehmann et al. | |
| 6,546,935 B2 | 4/2003 | Hooven | |
| 6,554,768 B1 | 4/2003 | Leonard | |
| 6,558,382 B2 | 5/2003 | Jahns et al. | |
| 6,575,969 B1 | 6/2003 | Rittman, III et al. | |
| 6,584,360 B2 | 6/2003 | Francischelli et al. | |
| 6,585,732 B2 | 7/2003 | Mulier | |
| 6,591,049 B2 | 7/2003 | Williams et al. | |
| 6,605,084 B2 | 8/2003 | Acker et al. | |
| 6,610,055 B1 | 8/2003 | Swanson et al. | |
| 6,610,060 B2 | 8/2003 | Mulier | |
| 6,613,048 B2 | 9/2003 | Mulier | |
| 6,632,222 B1 | 10/2003 | Edwards et al. | |
| 6,645,199 B1 | 11/2003 | Jenkins et al. | |
| 6,648,883 B2 | 11/2003 | Francischelli et al. | |
| 6,651,672 B2 | 11/2003 | Roth | |
| 6,656,175 B2 | 12/2003 | Francischelli et al. | |
| 6,663,626 B2 * | 12/2003 | Truckai et al. | 606/41 |
| 6,663,627 B2 | 12/2003 | Francischelli et al. | |
| 6,679,882 B1 | 1/2004 | Kornerup | |
| 6,692,450 B1 | 2/2004 | Coleman | |
| 6,692,491 B1 | 2/2004 | Phan | |
| 6,699,240 B2 | 3/2004 | Francischelli | |

| | | | |
|---|---|---|---|
| 6,702,811 B2 | 3/2004 | Stewart et al. | |
| 6,706,038 B2 | 3/2004 | Francischelli et al. | |
| 6,706,039 B2 | 3/2004 | Mulier et al. | |
| 6,716,211 B2 | 4/2004 | Mulier et al. | |
| 6,736,810 B2 | 5/2004 | Hoey et al. | |
| 6,755,827 B2 | 6/2004 | Mulier et al. | |
| 6,764,487 B2 | 7/2004 | Mulier et al. | |
| 6,773,433 B2 | 8/2004 | Stewart et al. | |
| 6,776,780 B2 | 8/2004 | Mulier et al. | |
| 6,802,840 B2 * | 10/2004 | Chin et al. | 606/41 |
| 6,807,968 B2 | 10/2004 | Francischelli et al. | |
| 6,827,715 B2 | 12/2004 | Francischelli et al. | |
| 6,849,073 B2 | 2/2005 | Hoey et al. | |
| 6,858,028 B2 | 2/2005 | Mulier et al. | |
| 6,887,238 B2 | 5/2005 | Jahns et al. | |
| 6,899,711 B2 | 5/2005 | Stewart et al. | |
| 6,911,019 B2 | 6/2005 | Mulier et al. | |
| 6,916,318 B2 | 7/2005 | Francischelli et al. | |
| 6,936,046 B2 | 8/2005 | Hissong | |
| 6,949,097 B2 | 9/2005 | Stewart et al. | |
| 6,949,098 B2 | 9/2005 | Mulier | |
| 6,960,205 B2 | 11/2005 | Jahns | |
| 6,962,589 B2 | 11/2005 | Mulier | |
| 7,056,329 B2 | 6/2006 | Kerr | |
| 7,507,235 B2 | 3/2009 | Keogh et al. | |
| 2001/0039419 A1 | 11/2001 | Francischelli et al. | |
| 2002/0009275 A1 | 1/2002 | Williams et al. | |
| 2002/0087183 A1 | 7/2002 | Boyd et al. | |
| 2002/0107517 A1 * | 8/2002 | Witt et al. | 606/50 |
| 2002/0120263 A1 * | 8/2002 | Brown et al. | 606/41 |
| 2002/0138109 A1 | 9/2002 | Keogh et al. | |
| 2003/0045872 A1 | 3/2003 | Jacobs et al. | |
| 2003/0144656 A1 | 7/2003 | Ocel et al. | |
| 2003/0163128 A1 | 8/2003 | Patil et al. | |
| 2003/0191462 A1 | 10/2003 | Jacobs et al. | |
| 2003/0216724 A1 | 11/2003 | Jahns | |
| 2004/0015106 A1 | 1/2004 | Coleman | |
| 2004/0015219 A1 | 1/2004 | Francischelli | |
| 2004/0044340 A1 | 3/2004 | Francischelli et al. | |
| 2004/0049179 A1 | 3/2004 | Francischelli et al. | |
| 2004/0078069 A1 | 4/2004 | Francischelli et al. | |
| 2004/0082948 A1 | 4/2004 | Stewart et al. | |
| 2004/0087940 A1 | 5/2004 | Jahns et al. | |
| 2004/0092926 A1 | 5/2004 | Hoey et al. | |
| 2004/0138621 A1 | 7/2004 | Jahns et al. | |
| 2004/0138656 A1 | 7/2004 | Francischelli et al. | |
| 2004/0143260 A1 | 7/2004 | Francischelli | |
| 2004/0186465 A1 | 9/2004 | Francischelli et al. | |
| 2004/0204734 A1 | 10/2004 | Wagner et al. | |
| 2004/0215183 A1 | 10/2004 | Hoey et al. | |
| 2004/0220560 A1 | 11/2004 | Briscoe | |
| 2004/0236322 A1 | 11/2004 | Mulier et al. | |
| 2004/0249368 A1 | 12/2004 | Hooven | |
| 2004/0267326 A1 | 12/2004 | Ocel | |
| 2005/0010095 A1 | 1/2005 | Stewart et al. | |
| 2005/0033280 A1 | 2/2005 | Francischelli et al. | |
| 2005/0090815 A1 | 4/2005 | Francischelli et al. | |
| 2005/0143729 A1 | 6/2005 | Francischelli et al. | |
| 2005/0165392 A1 | 7/2005 | Francischelli et al. | |
| 2005/0203561 A1 | 9/2005 | Palmer et al. | |
| 2005/0203562 A1 | 9/2005 | Palmer et al. | |
| 2005/0209564 A1 | 9/2005 | Bonner et al. | |
| 2005/0267454 A1 | 12/2005 | Hissong et al. | |
| 2006/0009756 A1 | 1/2006 | Francischelli et al. | |
| 2006/0009759 A1 | 1/2006 | Chrisitian et al. | |
| 2007/0043397 A1 | 2/2007 | Ocel | |

FOREIGN PATENT DOCUMENTS

| | | |
|---|---|---|
| EP | 0 450 608 | 10/1991 |
| EP | 0 765 639 | 4/1997 |
| EP | 1 095 627 | 5/2001 |
| WO | 92/05828 | 4/1992 |
| WO | 93/25267 | 12/1993 |
| WO | 97/10764 | 3/1997 |
| WO | 97/32525 | 9/1997 |
| WO | 98/17187 | 4/1998 |
| WO | 98/53750 | 12/1998 |
| WO | 99/02096 | 1/1999 |
| WO | 99/04696 | 2/1999 |

| | | |
|---|---|---|
| WO | 99/12487 | 3/1999 |
| WO | 99/44519 | 9/1999 |
| WO | 99/56486 | 11/1999 |
| WO | 99/56644 | 11/1999 |
| WO | 99/56648 | 11/1999 |
| WO | 99/59486 | 11/1999 |
| WO | 00/21449 | 4/2000 |
| WO | 00/27310 | 5/2000 |
| WO | 00/27311 | 5/2000 |
| WO | 00/27312 | 5/2000 |
| WO | 00/27313 | 5/2000 |
| WO | 00/42931 | 7/2000 |
| WO | 00/42932 | 7/2000 |
| WO | 00/42933 | 7/2000 |
| WO | 00/42934 | 7/2000 |
| WO | 01/80755 | 11/2001 |
| WO | 01/82812 | 11/2001 |
| WO | 01/82813 | 11/2001 |
| WO | 02/087454 | 11/2002 |

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.
Gallagher et al., "Cryosurgical Ablation of Accessory Atrioventrical Connections: A Method for Correction of the Pre-excitation Syndrome," Circulation 55(3): 471-479, 1977.
Sealy, "Direct Surgical Treatment of Arrhythmias: The Last Frontier in Surgical Cardiology," Chest 75(5): 536-537, 1979.
Sealy, "The Evolution of the Surgical Methods for Interruption of Right Free Wall Kent Bundles," The Annals of Thoracic Surgery 36(1): 29-36, 1983.
Guiraudon et al., "Surgical Repair of Wolff-Parkinson-White Syndrome: A New Closed-Heart Techique," The Annals of Thoracic Surgery 37(1): 67-71, 1984.
Klein et al., "Surgical Correction of the Wolff-Parkinson-White Syndrome in the Closed Heart Using Cryosurgery: A Simplified Approach," JACC 3(2): 405-409, 1984.
Randall et al., "Local Epicardial Chemical Ablation of Vagal Input to Sino-Atrial and Atrioventricular Regions of the Canine Heart," Journal of the Autonomic Nervous System 11:145-159, 1984.
Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.
Gallagher et al., "Surgical Treatment of Arrhythmias," The American Journal of Cardiology 61:27A-44A, 1988.
Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.
Cox et al., Surgery for Atrial Fibrillation; Seminars in Thoracic and Cardiovascular Surgery, vol. 1, No. 1 (Jul. 1989) pp. 67-73.
Bredikis and Bredikis; Surgery of Tachyarrhythmia: Intracardiac Closed Heart Cryoablation; PACE, vol. 13, pp. 1980-1984.
McCarthy et al., "Combined Treatment of Mitral Regurgitation and Atrial Fibrillation with Valvuloplasty and the Maze Procedure," The American Journal of Cardiology 71: 483-486, 1993.
Yamauchi et al. "Use of Intraoperative Mapping to Optimize Surgical Ablation of Atrial Flutter," The Annals of Thoracic Surgery 56: 337-342, 1993.
Graffigna et al., "Surgical Treatment of Wolff-Parkinson-White Syndrome: Epicardial Approach Without the Use of Cardiopulmonary Bypass," Journal of Cardiac Surgery 8: 108-116, 1993.
Siefert et al., "Radiofrequency Maze Ablation for Atrial Fibrillation," Circulation 90(4): 1-594.
Surgical treatment of atrial fibrillation: a review; Europace (2004) 5, S20-S29.
Elvan et al., "Radiofrequency Catheter Ablation of the Atria Reduces Inducibility and Duration of Atrial Fibrillation in Dog," Circulation 91: 2235-2244, 1995.
Cox et al., "Modification of the Maze Procedure for Atrial Flutter and Atrial Fibrillation. I. Rational and Surgical Results," The Journal of Thoracic Cardiovascular Surgery 110: 473-484, 1995.
Cox, "The Maze III Procedure for Treatment of Atrial Fibrillation," Sabiston DC, ed Atlas of Cardiothoracic Surgery, Philadelphia: WB Saunders: 460-475, 1994.
Sueda et al., "Simple Left Atrial Procedure for Chronic Atrial Fibrillation Associated with Mitral Valve Disease," The Annals of Thoracic Surgery 62(6): 1796-1800, 1996.
Tsui et al., "Maze 3 for Atrial Fibrillation: Two Cuts Too Few?" PACE 17: 2163-2166, 1994.
Kosakai et al., "Cox Maze Procedure for Chronic Atrial Fibrillation Associated with Mitral Valve Disease," The Journal of Thoracic Cardiovascular Surgery 108: 1049-1055, 1994.
Cox et al., "The Surgical Treatment of Atrial Fibrillation, IV Surgical Technique," *J of Thorac Cardiovasc Surg*, 1991: 101: 584-593.
Nardella, "Radio Frequency Energy and Impedance Feedback," SPIE vol. 1068, Catheter Based Sensing and Imaging Technology (1989).
Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.
Sie et al., "Radiofrequency Ablation of Atrial Fibrillation in Patients Undergoing Mitral Valve Surgery. First Experience," Circulation (Nov. 1996) 96:45,I-675,#3946.
Sie et al., "Radiofrequency Ablation of Atrial Fibrillation in Patients Undergoing Valve Surgery," Circulation (Nov. 1997) 84:I450,#2519.
Jais et al., "Catheter Ablation for Paroxysmal Atrial Fibrillation: High Success Rates with Ablation in the Left Atrium," Circulation (Nov. 1996) 94:I-675,#3946.
Cox, "Evolving Applications of the Maze Procedure for Atrial Fibrillation," Ann Thorac Surg, 1993;55:578-580.
Cox et al. "Five-Year Experience with the Maze Procedure for Atrial Fibrillation," Ann Thorac Surg, 1993; 56:814-824.
Avitall et al., "New Monitoring Criteria for Transmural Ablation of Atrial Tissues," Circulation, 1996;94(Supp 1):I-493, #2889.
Cox et al., "An 8 ½ Year Clinical Experience with Surgery for Atrial Fibrillation," Annals of Surgery, 1996;224(3):267-275.
Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.
Haissaguerre et al., "Right and Left Atrial Radiofrequency Catheter Therapy of Paroxysmal Atrial Fibrillation," Journal of Cardiovascular Electrophysiology, 1996;7(12):1132-1144.
Haissaguerre et al., "Role of Catheter Ablation for Atrial Fibrillation," Current Opinion in Cardiology, 1997;12:18-23.
Kawaguchi et al., "Risks and Benefits of Combined Maze Procedure for Atrial Fibrillation Associated with Organic Heart Disease," JACC, 1996;28(4):985-990.
Cox, et al., "Perinodal cryosurgery for atrioventricular node reentry tachycardia in 23 patients," Journal of Thoracic and Cardiovascular Surgery, 99:3, Mar. 1990, pp. 440-450.
Cox, "Anatomic-Electrophysiologic Basis for the Surgical Treatment of Refractory Ischemic Ventricular Tachycardia," Annals of Surgery, Aug. 1983; 198:2;119-129.
Williams, et al., "Left atrial isolation," J Thorac Cardiovasc Surg; 1980; 80: 373-380.
Scheinman, "Catheter-based Techniques for Cure of Cardiac Arrhythmias," Advances in Cardiovascular Medicine, 1996, ISSN 1075-5527, pp. 93-100.
Sueda et al., "Efficacy of a Simple Left Atrial Procedure for Chronic Atrial Fibrillation in Mitral Valve Operations," Ann Thorac Surg, 1997;63:1070-1075.

* cited by examiner

FLUID-ASSISTED ELECTROSURGICAL INSTRUMENT WITH SHAPEABLE ELECTRODE

BACKGROUND OF THE INVENTION

The present invention relates to an electrosurgical instrument and related system for use in surgical ablation or electrocautery procedures. More particularly, it relates to a fluid-assisted electrocautery instrument designed to be indifferent to rotational orientation and including a bendable shaft capable of independently maintaining a desired shape.

A wide variety of surgical procedures involve ablation or cauterization of selected tissue. For example, hemorrhoid or varicose vein removal can be accomplished by ablating the tissue in question. Additionally, tissue ablation and/or cauterization is commonly employed for the surgical treatment of cardiac arrhythmia, and in particular atrial fibrillation. In general terms, cardiac arrhythmia relates to disturbances in the heart's electrical system that causes the heart to beat irregularly, too fast or too slow. Irregular heartbeats, or arrhythmia, are caused by physiological or pathological disturbances in the discharge of electrical impulses from the sinoatrial node, in the transmission of the signal through heart tissue, or spontaneous, unexpected electrical signals generated within the heart. One type of arrhythmia is tachycardia, which is an abnormal rapidity of heart action. There are several different forms of atrial tachycardia, including atrial fibrillation and atrial flutter. With atrial fibrillation, instead of a single beat, numerous electrical impulses are generated by depolarizing tissue at one or more locations in the atria (or possible other locations). These unexpected electrical impulses produce irregular, often rapid heartbeats in the atrial muscles and ventricles. As to the location of the depolarizing tissue, it is generally agreed that the undesired electrical impulses often originate in the left atrial region of the heart, and in particular in one (or more) of the pulmonary veins extending from the left atrium. With this in mind, and as an alternative to drug therapy, ablation of the abnormal tissue or accessory pathway responsible for the atrial fibrillation has proven highly viable.

Regardless of exact application, ablation or cauterization of tissue is typically achieved by applying a destructive energy source to the target tissue, including radiofrequency electrical energy, direct current electrical energy, and the like. The ablative energy source is provided by an electrode that is otherwise placed in contact with the target tissue. For some treatments, the electrode can be formed as a part of a catheter that is otherwise sub-cutaneously delivered to the target site. While relatively non-invasive, catheter-based treatments present certain obstacles to achieving precisely located, complete ablation lesion patterns due to the highly flexible nature of the catheter itself, the confines of the surgical site; etc.

A highly viable alternative device is the hand-held electrosurgical instrument. As used herein, the term "electrosurgical instrument" includes a hand-held instrument capable of ablating tissue or cauterizing tissue, but does not include a catheter-based device. The instrument is relatively short (as compared to a catheter-based device), and rigidly couples the electrode tip to the instrument's handle that is otherwise held and manipulated by the surgeon. The rigid construction of the electrosurgical instrument requires direct, open access to the targeted tissue. Thus, for treatment of atrial fibrillation via an electrosurgical instrument, it is desirable to gain access to the patient's heart through one or more openings in the patient's chest (such as a sternotomy, a thoracotomy, a small incision and/or a port). In addition, the patient's heart may be opened through one or more incisions, thereby allowing access to the endocardial surface of the heart.

Once the target site (e.g., right atrium, left atrium, epicardial surface, endocardial surface, etc.) is accessible, the surgeon positions the electrode tip of the electrosurgical instrument at the target site. The tip is then energized, ablating (or for some applications, cauterizing) the contacted tissue. A desired lesion pattern is then created (e.g., portions of a known "Maze" procedure) by moving the tip in a desired fashion along the target site. In this regard, the surgeon can easily control positioning and movement of the tip, as the electrosurgical instrument is rigidly constructed and relatively short (in contrast to a catheter-based ablation technique).

Electrosurgical instruments, especially those used for the treatment of atrial fibrillation, have evolved to include additional features that provide improved results for particular procedures. For example, U.S. Pat. No. 5,897,553, the teachings of which are incorporated herein by reference, describes a fluid-assisted electrosurgical instrument that delivers a conductive solution to the target site in conjunction with electrical energy, thereby creating a "virtual" electrode. The virtual electrode technique has proven highly effective in achieving desired ablation while minimizing collateral tissue damage. Other electrosurgical instrument advancements have likewise optimized system performance. However, a common characteristic associated with available electrosurgical instruments is a "designed-in" directional orientation. That is to say, electrosurgical devices, and especially those used for atrial fibrillation treatment procedures, are curved along a length thereof, as exemplified by the electrosurgical instrument of U.S. Pat. No. 5,897,553. In theory, this permanent curved feature facilitates the particular procedure (or lesion pattern) for which the electrosurgical instrument is intended. Unfortunately, however, the actual lesion pattern formation technique and/or bodily structure may vary from what is expected, so that the curve is less than optimal. Additionally, the premade curve may be well suited for one portion of a particular procedure (e.g., right atrium ablation pattern during the Maze procedure), but entirely inapplicable to another portion (e.g., left atrium ablation during the Maze procedure). As a result, the electrosurgical instrument design may actually impede convenient use by a surgeon.

Electrosurgical instruments continue to be highly useful for performing a variety of surgical procedures, including surgical treatment of atrial fibrillation. While certain advancements have improved overall performance, the accepted practice of imparting a permanent curve or other shape variation into the instrument itself may impede optimal usage during a particular procedure. Therefore, a need exists for an electrosurgical instrument that, as initially presented to a surgeon, is indifferent to rotational orientation, and further is capable of independently maintaining a number of different shapes as desired by the surgeon.

SUMMARY OF THE INVENTION

One aspect of the present invention relates to an electrosurgical instrument including an elongated shaft and a non-conductive handle. The shaft defines a proximal section, a distal section, and an internal lumen extending from the proximal section. The distal section forms an electrically conductive rounded tip and defines at least one passage fluidly connected to the lumen. This passage distributes fluid from the internal lumen outwardly from the shaft. Further, the shaft is adapted to be transitionable from a straight state to a bent state, preferably a number of different bent states. In this regard, the shaft is capable of independently maintaining the distinct shapes associated with the straight state and the bent state(s). The non-conductive handle is rigidly coupled to the proximal section of the shaft. With this in mind, an exterior surface of the shaft distal the handle and proximal the distal section is electrically non-conductive. In one preferred embodiment, the shaft is comprised of an elongated electrode body and an electrical insulator. The electrode body defines the distal section and is rigidly coupled to the handle. The electrical insulator surrounds at least a portion of the electrode body proximal the distal section such that the tip is exposed.

During use, and when first presented to a surgeon, the shaft is in the straight state such that the electrosurgical instrument is effectively indifferent to a rotational orientation when the handle is grasped by the surgeon. Subsequently, the surgeon can bend the shaft to a desired shape (i.e., the bent state) being most useful for the particular electrosurgical procedure. During the procedure, a conductive fluid is directed onto the target site from the internal lumen via the passage. The tip then energizes the dispensed fluid, causing tissue ablation or cauterization.

Yet another aspect of the present invention relates to an electrosurgical system including an electrosurgical instrument, a source of conductive fluid, and an energy source. The electrosurgical instrument includes an elongated shaft and a non-conductive handle. The shaft defines a proximal section, a distal section, and an internal lumen extending from the proximal section. The distal section forms an electrically conductive rounded tip and defines at least one passage fluidly connected to the lumen. Further, the shaft is adapted to be transitionable from, and independently maintain a shape in, a straight state and a bent state. The handle is rigidly coupled to the proximal section of the shaft. An exterior surface of the shaft distal the handle and proximal the distal section is electrically non-conductive. The source of conductive fluid is fluidly connected to the internal lumen. Finally, the energy source is electrically connected to the tip. During use, the electrosurgical instrument can be presented to the target site in either the straight state or the bent state. Regardless, the shaft independently maintains the shape associated with the selected state. Conductive fluid is delivered from the conductive fluid source to the internal lumen, and is then distributed to the target site via the passage. The energy source is activated, thereby energizing the electrode tip. This action, in turn, energizes the distributed conductive fluid, causing desired tissue ablation or cauterization. In one preferred embodiment, the electrosurgical instrument further includes an indifferent, or non-ablating, electrode (such as a grounding patch). The indifferent electrode is electrically connected to the energy source and it is placed separately from the target site. For example, the indifferent electrode may be placed on the back of the patient.

Yet another aspect of the present invention relates to a method of performing an electrosurgical procedure. The method includes providing an electrosurgical instrument including an elongated shaft and, a handle. In this regard, the shaft defines a proximal section, a distal section, and an internal lumen. The proximal section is rigidly coupled to the handle, whereas the distal section forms a round tip. Finally, the internal lumen extends from the proximal section and is in fluid communication with at least one passage formed in the distal section. An exterior surface of the shaft distal the handle and proximal the distal section is electrically non-conductive. The shaft is provided in an initial straight state that otherwise defines a linear axis. The shaft is then bent to a first bent state in which a portion of the shaft is deflected relative to the linear axis. In this regard, the shaft independently maintains a shape of the first bent state. The tip is then positioned at a tissue target site. In one preferred embodiment, an indifferent electrode is placed in contact with the patient. Conductive fluid is dispensed from the passage to the tissue target site via the internal lumen. Finally, energy is applied to the dispensed fluid by energizing the tip. Subsequently, the energized tip and conductive fluid ablates or cauterizes tissue at the tissue target site. In one embodiment, the tissue target site comprises tissue of a patient's heart, and the method further includes accessing the tissue target site through one or more openings in the patient's chest. In another embodiment, after a first lesion pattern is formed at a first tissue target site, the shaft is bent to a second shape and the procedure repeated to effectuate a second lesion pattern at a second tissue target site.

DESCRIPTION OF THE PREFERRED EMBODIMENTS

Figure 1:
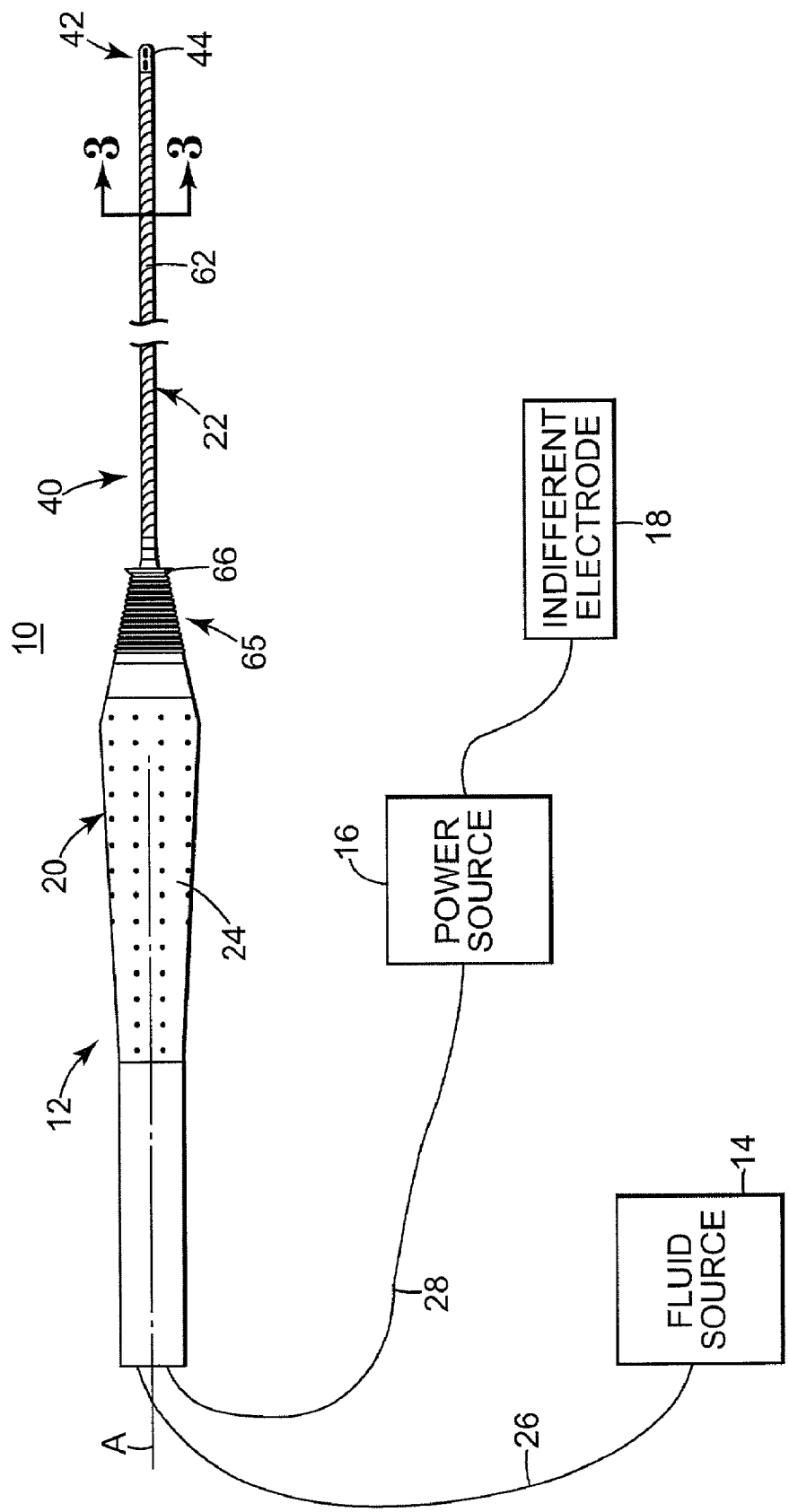
FIG. 1 is a side view of an electrosurgical system in accordance with the present invention, including portions shown in block form.

One preferred embodiment of an electrosurgical system 10 in accordance with the present invention is shown in FIG. 1. The system 10 is comprised of an electrosurgical instrument 12, a fluid source 14, a power source 16, and an indifferent electrode 18. The various components are described in greater detail below. In general terms, however, the fluid source 14 is fluidly connected to the electrosurgical instrument 12. Similarly, the power source 16 is electrically connected to the electrosurgical instrument 12 and to the indifferent electrode 18. During use, conductive fluid is delivered from the fluid source 14 to a distal portion of the electrosurgical instrument 12. The distributed fluid is energized by the electrosurgical instrument 12 via the power source 16. The so-energized conductive fluid is capable of forming a virtual electrode, which is capable of ablating or cauterizing contacted tissue.

Figure 5A:
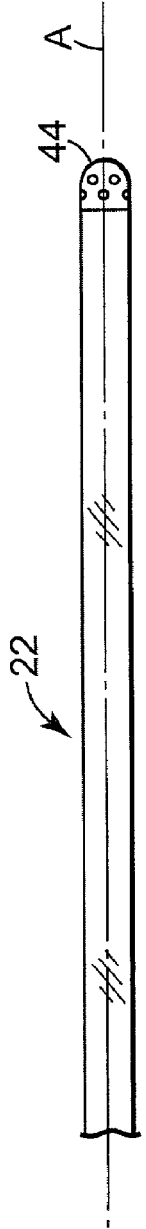
FIGS. 5A-5C are side views of the electrosurgical instrument of FIG. 1, illustrating exemplary shapes available during use of the electrosurgical instrument.
Figure 5B:
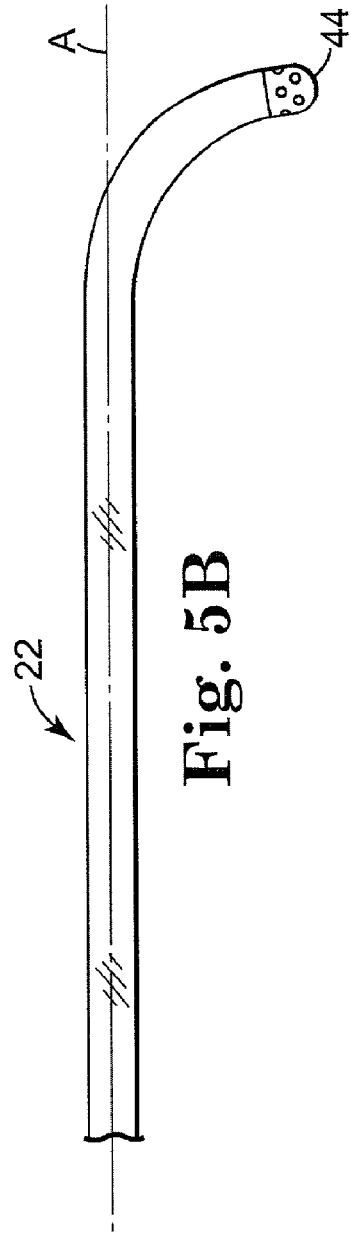
Figure 5C:
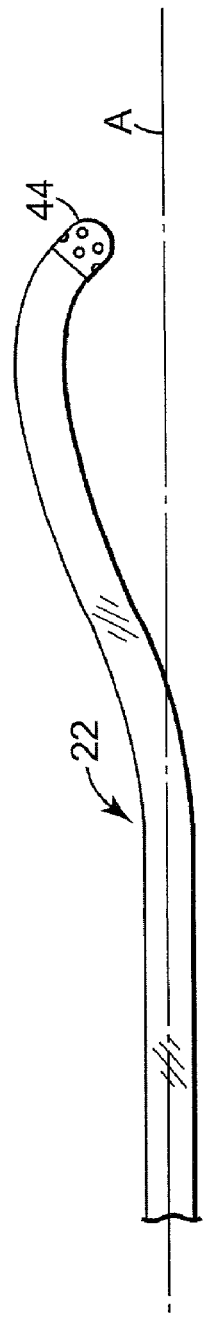

The electrosurgical instrument 12 includes a handle 20 and a shaft 22. As described in greater detail below, the shaft 22 is rigidly coupled to the handle 20, and is transitionable from a straight state (as illustrated in FIG. 1) to a bent state (for example as shown in FIGS. 5B and 5C). In this regard, the shaft 22 independently maintains the shape associated with the particular state (i.e., straight or bent).

The handle 20 is preferably made of a sterilizable, rigid, and non-conductive material, such as a polymer or ceramic. Suitable polymers include rigid plastics, rubbers, acrylics, nylons, polystyrenes, polyvinylchlorides, polycarbonates, polyurethanes, polyethylenes, polypropylenes, polyamides, polyethers, polyesters, polyolefins, polyacrylates, polyisoprenes, fluoropolymers, combinations thereof or the like. Further, the handle 20 is ergonomically designed to comfortably rest within a surgeon's hand (not shown). To this end, the handle 20 may include a grip portion 24 that is circular in cross section. This configuration facilitates grasping of the handle 20, and thus of the electrosurgical instrument 12, at any position along the grip portion 24 regardless of an overall rotational orientation of the electrosurgical instrument 12. That is to say, due to the circular, cross-sectional shape of the grip portion 24, the electrosurgical instrument 12 can be rotated to any position relative to a central axis A, and still be conveniently grasped by the surgeon. In an even more preferred embodiment, the grip portion 24 defines a gradual, distally increasing diameter that provides an orientation feature to help a surgeon identify where along the length of the electrosurgical instrument 12 he or she is grasping. For example, if the surgeon grasps the electrosurgical instrument 12 out of his visual sight during a medical procedure, the surgeon may identify based on the grip portion's 24 diameter where along the instrument he has grasped. Finally, the grip portion 24 is preferably formed of a low durometer polymer. Suitable polymers include low durometer plastics, rubbers, silicones, acrylics, nylons, polystyrenes, polyvinylchlorides, polycarbonates, polyurethanes, polyethylenes, polypropylenes, polyamides, polyethers, polyesters, polyolefins, polyacrylates, polyisoprenes, fluoropolymers, combinations thereof or the like. The grip portion 24 alternatively may be a sponge-like or foam-like material, such as an open-cell material or a closed-cell material.

Figure 2:
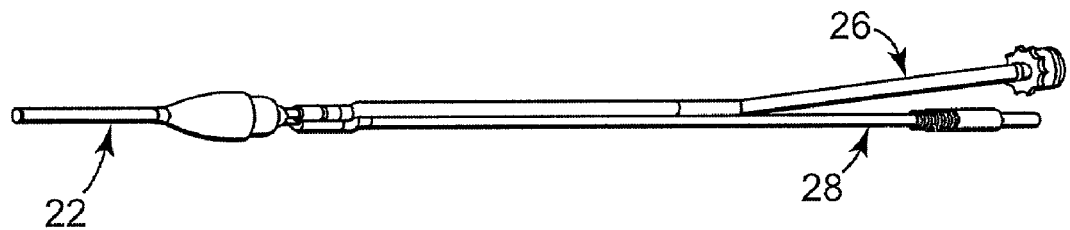
FIG. 2 is a perspective view of an electrosurgical instrument portion of the system of FIG. 1, with a handle removed.

Regardless of exact configuration, the handle 20 forms or encompasses one or more central lumens (not shown). The lumen(s) provides a pathway for a line or tubing 26 from the fluid source 14 to the shaft 22, as well as a pathway for a line or wiring 28 from the power source 16 to the shaft 22. In this regard, FIG. 2 illustrates the electrosurgical instrument 12 with the handle 20 removed. The tubing 26 from the fluid source 14 (FIG. 1) is shown as extending to, and being fluidly connected with, the shaft 22. Similarly, the line 28 from the power source 16 (FIG. 1) is shown as extending to, and being electrically connected with, the shaft 22.

Returning to FIG. 1, the shaft 22 is an elongated, relatively rigid component defining a proximal section 40 and a distal section 42. The distal section 42 terminates in an electrically conductive tip 44. As described in greater detail below, the tip 44 is rounded, defining a uniform radius of curvature. With this configuration, the tip 44 is, similar to the handle 20, indifferent to rotational orientation of the electrosurgical device 12. That is to say, regardless of how a surgeon (not shown) grasps the handle 20 (i.e., the rotational position of the handle 20 relative to the central axis A), a profile of the tip 44 in all directions (e.g., in front of the surgeon's thumb position, behind the surgeon's thumb position, etc.) is always the same so that the tip 44 is readily maneuvered along tissue (not shown) in any direction. To this end, the rounded shape facilitates sliding movement of the tip 44 along the tissue.

Figure 3:
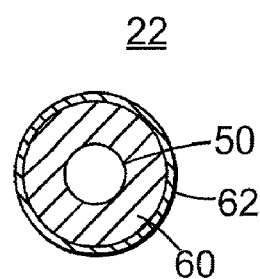
FIG. 3 is an enlarged, cross-sectional view of a portion of an electrosurgical instrument of FIG. 1 taken along the line 3-3.

With additional reference to FIG. 3, the shaft 22 defines an internal lumen 50 that is fluidly connected to the tubing 26. In this way, the internal lumen 50 delivers fluid from the fluid source 14 to the distal section 42.

Figure 4A:
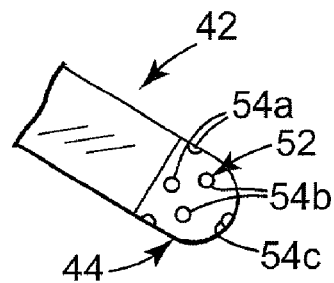
FIG. 4A is an enlarged, perspective view of a distal portion of the electrosurgical instrument of FIG. 1.

With additional reference to FIG. 4A, the distal section 42 preferably forms a plurality of passages 52 that are fluidly connected to the internal lumen 50. The passages 52 are formed at or proximal the tip 44 and preferably are uniformly located relative to a circumference of the distal section 42. For example, in one preferred embodiment, two sets 54a, 54b of the passages 52 are provided, in addition to a central passage 54c at the tip 44. The passages 52 associated with each of the two sets 54a, 54b are circumferentially aligned, and uniformly spaced approximately 90° from one another. For example, in one embodiment, the passages 52 are uniformly located on a hemispherical portion of the tip 44 as described below. Alternatively, other numbers and locations are acceptable. By preferably uniformly spacing the passages 52, however, the distal section 42 is further formed to be indifferent to rotational orientation of the electrosurgical instrument 12. In other words, regardless of the rotational position of the electrosurgical instrument 12 and/or the direction of tip 44 movement, the passages 52 provide a relatively uniform disbursement of conductive fluid about the tip 44 via the internal lumen 50. In an alternative embodiment, the tip 44 is made of a porous material, that allows fluid to pass from the internal lumen 50 through the tip 44.

Figure 4B:
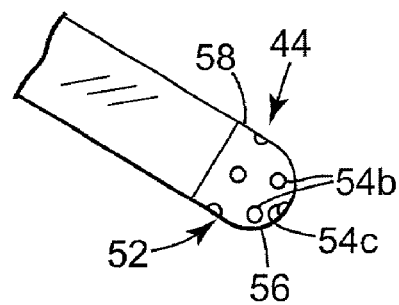
FIG. 4B is an enlarged, perspective view of a distal portion of an alternative embodiment electrosurgical instrument in accordance with the present invention.

In another alternative embodiment, and as best shown in FIG. 4B, at least some of the passages 52 (for example, the passage set 54b) are located along a generally hemispherical portion 56 of the tip 44. This one preferred design facilitates a more complete delivery of liquid to a target site (not shown) that is otherwise contacted by the tip 44. In general terms, during an electrosurgical procedure, it is important that a sufficient volume of irrigation fluid is continually provided to the electrode tip 44/target site tissue interface to reduce the opportunity for tissue charring or desiccation. Previous electrosurgical designs positioned all of the passages 52 (except for the central passage 54c) along a cylindrical portion 58 of the tip 44 (as opposed to the generally hemispherical portion 56). With this prior design, where a particular surgical procedure required that the tip 44 be oriented such that the passages 52 are "below" the electrode tip 44/target site tissue interface, some or all of the irrigation liquid otherwise dispensed from the passages 52 (other than the central passage 54c) might flow away from the electrode tip 44 (or back along the shaft 22). The one preferred passage configuration of FIG. 4B overcomes this concern, as all of the irrigation liquid distributed from the passages 54b on the generally hemispherical portion 56 will be delivered to the electrode tip 44/target site tissue interface due to surface tension at the interface.

Regardless of passage location, a further preferred feature of the shaft 22 is a malleable or shapeable characteristic. In particular, and with additional reference to FIGS. 5A-5C, the shaft 22 is configured to be transitionable from an initial straight state (FIG. 5A) to a bent or curved state (FIGS. 5B and 5C). In this regard, the electrosurgical instrument 12, and in particular the shaft 22, is initially presented to a surgeon (not shown) in the straight state of FIG. 5A, whereby the shaft 22 assumes a straight shape defining the central axis A. In the straight state, the shaft 22 is indifferent to rotational orientation, such that the electrosurgical instrument 12 can be grasped at any rotational position and the tip 44 will be located at an identical position. Further, as previously described, a profile of the tip 44 is also uniform or identical at any rotational position of the electrosurgical instrument 12. Subsequently, depending upon the constraints of a particular electrosurgical procedure, the shaft 22 can be bent relative to the central axis A. Two examples of an applicable bent state or shape are provided in FIGS. 5B and 5C. In a preferred embodiment, the shaft 22 can be bent at any point along a length thereof, and can be formed to include multiple bends or curves. Regardless, the shaft 22 is configured to independently maintain the shape associated with the selected bent shape. That is to say, the shaft 22 does not require additional components (e.g., pull wires, etc.) to maintain the selected bent shape. Further, the shaft 22 is constructed such that a user can readily re-shape the shaft 22 back to the straight state of FIG. 5A and/or other desired bent configurations. Notably, the shaft 22 is configured to relatively rigidly maintain the selected shape such that when a sliding force is imparted onto the shaft 22 as the tip 44 dragged across tissue, the shaft 22 will not overtly deflect from the selected shape.

In one preferred embodiment, the above-described characteristics of the shaft 22 are achieved by forming the shaft 22 to include an elongated electrode body 60 and an electrical insulator covering 62 as shown in FIGS. 1 and 3. The electrode body 60 defines the proximal section 40 and the distal section 42 of the shaft 22. To this end, the proximal section 40 of the electrode body 60 is rigidly coupled to the handle 20. The insulator 62 covers a substantial portion of the electrode body 60, preferably leaving the distal section 42 exposed. In particular, the insulator 62 is positioned to encompass an entirety of the electrode body 60 distal the handle 20 and proximal the distal section 42 (and in particular, proximal the passages 52 and the tip 44).

In one preferred embodiment, the electrode body 60 is a tube formed of an electrically conductive, malleable material, preferably stainless steel, however other materials such as, for example, nitinol can be used. The passages 52 are preferably drilled, machined, laser cut, or otherwise formed through at least a portion of the electrode body 60. The passages or openings 52 may comprise circular holes, semi-circular holes, oval holes, rectangular slots, and/or other configurations for allowing fluid to pass.

The insulator 62 is formed of one or more electrically non-conductive materials, and serves to electrically insulate the encompassed portion of the electrode body 60. Multiple layers of electrically non-conductive materials can help prevent the likelihood of forming an electrical short along the length of the electrode body 60 due to a mechanical failure of one of the non-conductive materials. In this regard, the insulator 62 is preferably comprised of two materials having considerably different mechanical properties, e.g., a silicone and a fluoropolymer. In one preferred embodiment, a silicone tubing material is overlaid with a heat shrink fluoropolymer tubing material. Alternatively, the insulator 62 may be one or more non-conductive coatings applied over a portion of the electrode body 60. In addition to being non-conductive, the insulator 62 is preferably flexible and conforms to the electrode body 60 such that the insulator 62 does not impede desired shaping and re-shaping of the electrode body 60 as previously described.

It will be understood that the preferred construction of the shaft 22 to include the elongated electrode body 60 and the insulator 62 is but one available configuration. Alternatively, the shaft 22 can be constructed of an electrode material forming the tip 44, and a rigid or malleable, non-conductive tube rigidly connecting the tip 44 to the handle 20. The non-conductive tube can include one or more metal conductors, such as straight wire and/or windings for electrically connecting the tip 44 to the power source 16. Along these same lines, another alternative embodiment includes forming the tip 44 from an inherently porous material. For example, the tip 44 may comprise one or more porous polymers, metals, or ceramics. Further, the tip 44 may be coated with non-stick coatings such as PTFE or other types of coatings such as biological coatings. Another alternative embodiment includes construction of the shaft 22 to include one or more metal conductors, such as straight wire and/or windings inside a rigid or malleable non-conductive polymer tube. The non-conductive polymer tube includes one or more openings, such as holes, slots or pores (preferably corresponding with the passages 52 previously described), which allow conductive fluid to exit the polymer tube. The conductive fluid creates a virtual electrode via electrically connecting the one or more metal conductors to the target tissue. Conversely, the shaft 22 may comprise a polymer tube having one or more openings, such as holes, slots or pores (preferably corresponding with the passages 52 previously described), placed inside an electrical conductor, such as a metal tube having one or more openings, such as holes, slots or pores, or a metal winding having a spacing that allows conductive fluid to pass through, to control conductive fluid delivery through the electrical conductor. Finally, the insulator 62 may cover a portion of the metal tube or windings.

Figure 6:
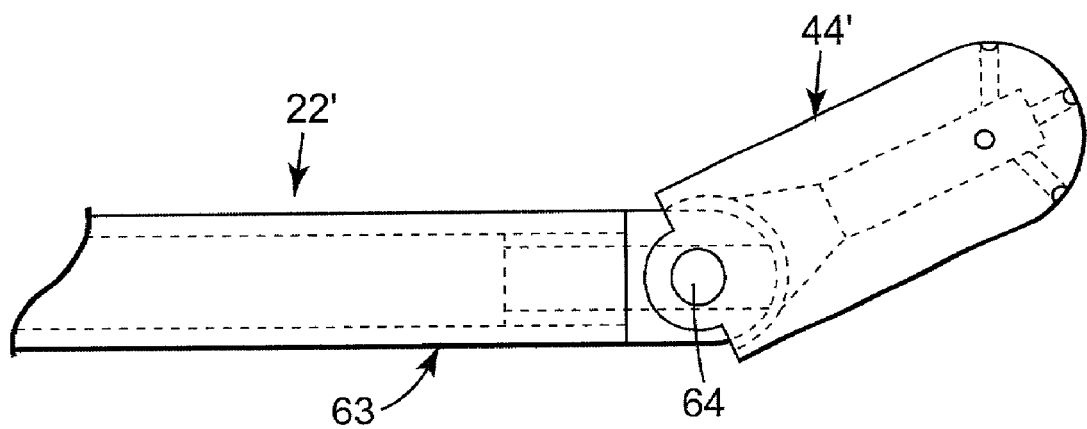
FIG. 6 is an enlarged, side view of a portion of an alternative embodiment electrosurgical instrument in accordance with the present invention.

With respect to the above-described alternative embodiments, connection between the elongated tube and the separate tip 44 can be accomplished in a variety of manners. Once again, the elongated tube can comprise a conductive or non-conductive material(s), such as metal(s) or plastic(s). The elongated tube can be connected to the tip 44 via a variety of coupling techniques, including, for example, welding, laser welding, spin welding, crimping, gluing, soldering and press fitting. Alternatively, the distal end of the elongated tube and the tip 44 can be configured to threadably engage one another and/or mechanical engagement member(s) (e.g., pins, screws, rivets, etc.) can be employed. In another embodiment, the elongated tube is rigidly coupled to the tip 44. In yet another embodiment, the tip 44 can be moveably coupled to the elongated tube, whereby the tip 44 can be moved and/or locked relative to the elongated tube. For example, the tip 44 can be coupled to the elongated tube via one or more joints or hinges. The joints or hinges can be ball joints and/or joints that include a pin. To this end, a pin-type joint can be configured to allow the tip 44 to swivel relative to the elongated tube. Further, the joint(s) can be configured to move and lock into position. In addition, one or more actuators (e.g., knobs, buttons, levers, slides, etc.) can be located on, for example, the handle 20 (FIG. 1) for actuating the joint(s). With the above in mind, FIG. 6 illustrates a portion of an alternative embodiment shaft 22' including a tip 44' moveably coupled to an elongated tube 63 by a pin 64.

Returning to FIG. 1, the electrosurgical instrument 12 preferably includes a coupling member 65 for rigidly coupling the shaft 22 to the handle 20. The coupling member 65 can comprise one or more polymers, plastics, and/or rubbers. For example, the coupling member 65 can comprise one or more silicones, acrylics, nylons, polystyrenes, polyvinylchlorides, polycarbonates, polyurethanes, polyethylenes, polypropylenes, polyamides, polyethers, polyesters, polyolefins, polyacrylates, polyisoprenes, fluoropolymers, combinations thereof or the like. The coupling member 65 preferably forms a drip edge 66 to interrupt, divert and prevent any flow of liquid from the tip 44, down the shaft 22 and onto the handle 20, thereby preventing any electrically conducting fluid from contacting the surgeon.

Regardless of exact construction of the electrosurgical instrument 12, the fluid source 14 maintains a supply of conductive fluid (not shown), such as an energy-conducting fluid, an ionic fluid, a saline solution, a saturated saline solution, a Ringer's solution, etc. It is preferred that the conductive fluid be sterile. The conductive fluid can further comprise one or more contrast agents, and/or biological agents such as diagnostic agents, therapeutic agents or drugs. The biological agents may be found in nature (naturally occurring) or may be chemically synthesized.

As a point of reference, during use the conductive fluid serves to electrically couples the electrode tip 44 of electrosurgical instrument 12 to the tissue to be treated, thereby lowering the impedance at the target site. The conductive fluid may create a larger effective electrode surface. The conductive fluid can help cool the tip 44 of the electrosurgical instrument 12. The conductive fluid may keep the surface temperature of the tip 44 below the threshold for blood coagulation, which may clog the electrosurgical instrument 12. The conductive fluid may also cool the surface of the tissue thereby preventing over heating of the tissue which can cause popping, desiccation, burning and/or charring of the tissue. The burning and/or charring of the tissue may also clog the electrosurgical instrument 12. Therefore, use of the conductive fluid may reduce the need to remove a clogged electrosurgical instrument for cleaning or replacement. Further, charred tissue has high impedance, thereby making the transfer of RF energy difficult, and may limit the ability of the electrosurgical instrument 12 to form a transmural lesion. The delivery of conductive fluid during the electrosurgical process may help create deeper lesions that are more likely to be transmural. Transmurality is achieved when the full thickness of the target tissue is ablated. Continuous conductive fluid flow may ensure that a conductive fluid layer between the tip 44 and the contours of the tissue to be treated is created.

In one preferred embodiment, the fluid source 14 includes a fluid reservoir, such as a bag, a bottle or a canister, for maintaining a supply of conductive fluid previously described. With this configuration, the fluid reservoir can be positioned at an elevated location, thereby gravity feeding the conductive fluid to the electrosurgical instrument 12, or the fluid reservoir may be pressurized, thereby pressure feeding the conductive fluid to the electrosurgical instrument 12. For example, a pressure cuff may be placed around a flexible bag, such as an IV bag, of conductive fluid, thereby pressure feeding the conductive fluid to the electrosurgical instrument 12. Alternatively, the fluid source 14 can include, and/or be connected to, a manual or electrical pump (not shown), such as an infusion pump, a syringe pump, or a roller pump. The fluid source 14 can further comprise one or more orifices or fluid regulators, (e.g., valves, fluid reservoirs, conduits, lines, tubes and/or hoses) to control flow rates. The conduits, lines, tubes, or hoses may be flexible or rigid. For example, a flexible hose may be used to communicate fluid from the fluid source 14 to the electrosurgical instrument 12, thereby allowing electrosurgical instrument 12 to be easily manipulated by a surgeon. Alternatively, the fluid source 14 can be directly connected to, or incorporated into, the handle 20. For example, a pressurized canister of conductive fluid may be directly connected to the handle 20. Further, the fluid source 14 can comprise a syringe, a squeeze bulb and/or some other fluid moving means, device or system.

In another embodiment, the fluid source 14 further includes a surgeon-controlled switch (not shown). For example, a switch may be incorporated in or on the fluid source 14 or any other location easily and quickly accessed by a surgeon for regulation of conductive fluid delivery. The switch may be, for example, a hand switch, a foot switch, or a voice-activated switch comprising voice-recognition technologies.

In yet another alternative embodiment, the fluid source 14 includes a visual and/or audible signaling device (not shown) used to alert a surgeon to any change in the delivery of conductive fluid. For example, a beeping tone or flashing light can be used to alert the surgeon that a change has occurred in the delivery of conductive fluid.

The power source 16 is of a type known in the art, and is preferably a radio-frequency (RF) generator. The generator can be powered by AC current, DC current or it can be battery powered either by a disposable or re-chargeable battery. The generator can incorporate a controller (not shown) or any suitable processor to control power levels delivered to the electrosurgical instrument 12 based on information supplied to the generator/controller.

The above-described electrosurgical system 10, including the electrosurgical instrument 12, is useful for a number of different tissue ablation and cauterization procedures. For example, the electrosurgical system 10 can be used to remove hemorrhoids or varicose veins or stop esophageal bleeding to name but a few possible uses. Additionally, the electrosurgical system 10 is highly useful for the surgical treatment of cardiac arrhythmia, and in particular treatment of atrial fibrillation via ablation of atrial tissue. To this end, the Maze procedure, such as described in *Cardiovascular Device Update*, Vol. 1, No. 4, July 1995, pp. 2-3, the teachings of which are incorporated herein by reference, is a well known technique, whereby lesion patterns are created along specified areas of the atria. The Maze III procedure, a modified version of the original Maze procedure, has been described in *Cardiac Surgery Operative Technique*, Mosby Inc., 1997, pp. 410-419, the teachings of which are incorporated herein by reference. In an effort to reduce the complexity of the surgical Maze procedure, a modified Maze procedure was developed as described in *The Surgical Treatment of Atrial Fibrillation*, Medtronic Inc., 2001, the teachings of which are incorporated herein by reference.

Figure 7A:
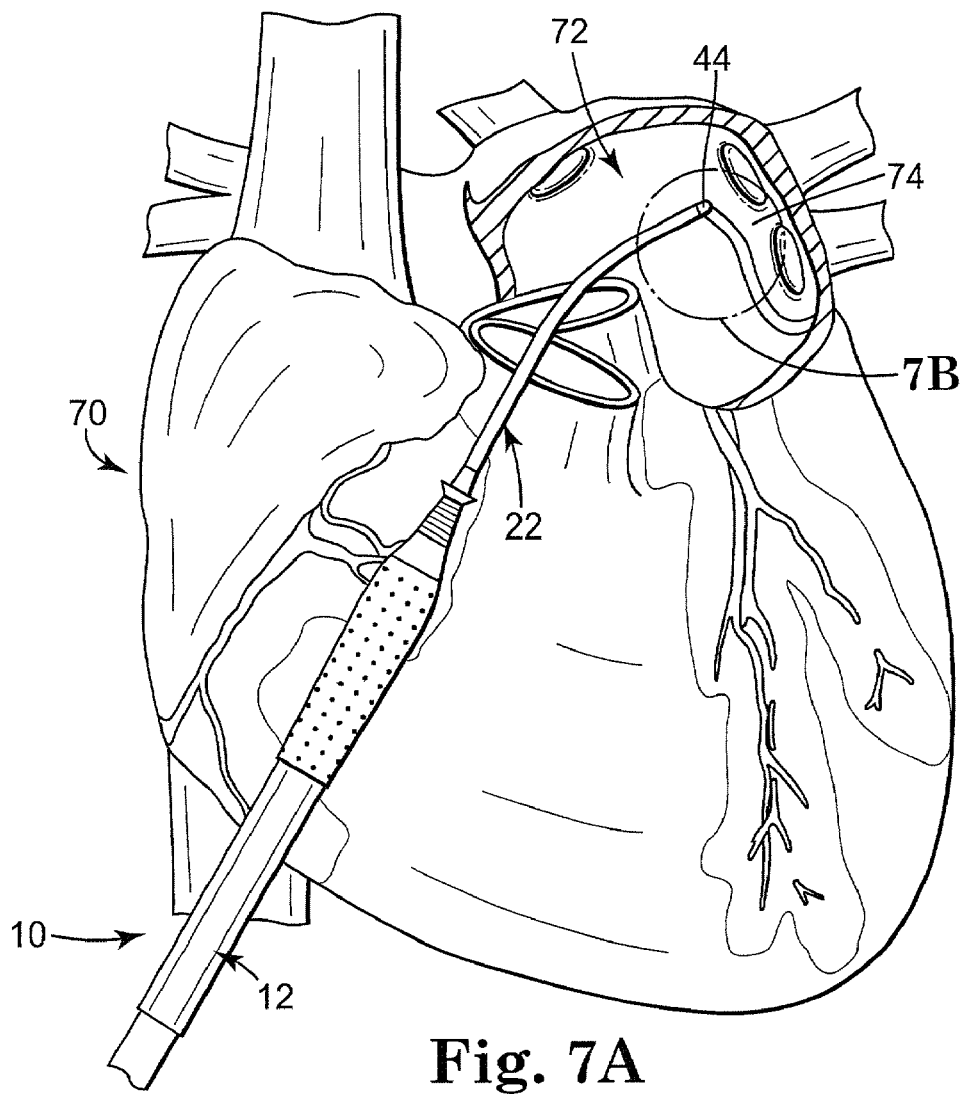
FIG. 7A is cut-away illustration of a patient's heart depicting use of an electrosurgical instrument in accordance with the present invention during a surgical ablation procedure.

FIG. 7A depicts use of the electrosurgical system 10, and in particular the electrosurgical instrument 12, performing a portion of the Maze procedure. In particular, FIG. 7A includes a representation of a heart 70 with its left atrium 72 exposed. Prior to use, the electrosurgical instrument 12 is provided to the surgeon (not shown) with the shaft 22 in the initial straight state (FIG. 1). The surgeon then evaluates the constraints presented by the tissue target site 74 and the desired lesion pattern to be formed. Following this evaluation, the surgeon determines an optimal shape of the shaft 22 most conducive to achieving the desired ablation/lesion pattern. With this evaluation in mind, the surgeon then transitions or bends the shaft 22 from the initial straight state to the bent state illustrated in FIG. 7A. Once again, the shaft 22 is configured to independently maintain this selected shape. The shaft 22 can be bent by hand and/or by use of bending jigs or tools.

Figure 7B:
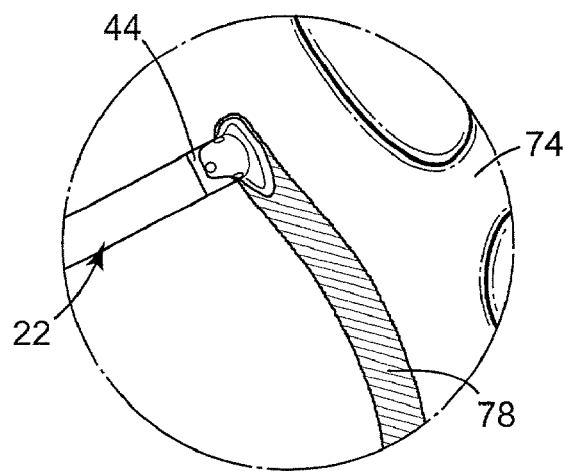
FIG. 7B is an enlarged illustration of a portion of FIG. 7A.

Once the desired shape of the shaft 22 has been achieved, the tip 44 is directed to the tissue target site 74. An indifferent electrode (18 in FIG. 1, but not shown in FIG. 7A) is placed in contact with the patient. Conductive fluid from the fluid source 14 (FIG. 1) is delivered to the tissue target site 74 via the internal lumen 50 (FIG. 3), the passages 52 and/or the porous tip 44. Once sufficient fluid flow has been established, the tip 44 is energized via the power source 16 (FIG. 1). The tip 44, in turn, energizes the distributed fluid, thereby creating a virtual electrode that ablates contacted tissue. The surgeon then slides or drags the tip 44 along the left atrium 70 tissue, thereby creating a desired lesion pattern 78, as best shown in FIG. 7B. In this regard, the rigid coupling between the shaft 22 and the handle 20 allows the tip 44 to easily be slid along the atrial tissue via movement of the handle 20. Once the desired lesion pattern 78 has been completed, energization of the tip 44 is discontinued, as well as delivery of conductive fluid from the fluid source 14. If additional lesion patterns are required, the surgeon again evaluates the target tissue site, and re-forms the shaft 22 accordingly.

Notably, the shaft 22 need not necessarily be bent to perform a tissue ablation procedure. Instead, the tip 44 can be drug across the target site tissue 74 with the shaft 22 in the initial straight state. In this regard, because the shaft 22 is straight and the handle 20 (FIG. 1) is preferably circumferentially uniform, the electrosurgical instrument 12 does not have a discernable drag direction (as compared to the shaft 22 being bent or curved, whereby the curve inherently defines a most appropriate drag direction).

In addition to the one exemplary procedure described above, the electrosurgical instrument 12 may be positioned and used, for example, through a thoracotomy, through a sternotomy, percutaneously, transveneously, arthroscopically, endoscopically, for example, through a percutaneous port, through a stab wound or puncture, through a small incision, for example, in the chest, in the groin, in the abdomen, in the neck or in the knee, or in combinations thereof. It is also contemplated that the electrosurgical instrument 12 may be used in other ways, for example, in open-chest surgery on a heart in which the sternum is split and the rib cage opened with a retractor.

The electrosurgical system 10, and in particular the electrosurgical instrument 12, described above with respect to FIG. 1 is but one acceptable configuration in accordance with the present invention. That is to say, the system 10 and/or the instrument 12 can assume other forms and/or include additional features while still providing an electrosurgical instrument having a shaft that independently maintains varying shapes associated with a straight state and a bent state, and is indifferent to rotational orientation in the straight state.

For example, the electrosurgical instrument 12 can include a surgeon-controlled switch. For example, a switch may be incorporated in or on the electrosurgical instrument 12 or any other location easily and quickly accessed by the surgeon for regulation of the electrosurgical instrument 12 by the surgeon. The switch may be, for example, a hand switch, a foot switch, or a voice-activated switch comprising voice-recognition technologies. One or more switches may be incorporated into the grip portion 24 of the electrosurgical instrument 12. For example, a switch may be used to control conductive fluid delivery and/or power delivery. A switch incorporated into the grip portion 24 may be a switch, such as a membrane switch, encompassing the entire circumference of the electrosurgical instrument 12, thereby effectively being indifferent to a rotational orientation when the surgeon grasps the handle. That is to say, due to the cross-sectional shape of the switch, the electrosurgical instrument 12 may be rotated to any position relative to a central axis A, and still be conveniently controlled by the surgeon.

Alternatively, a hand switch connected to the electrosurgical instrument 12, but not incorporated into the electrosurgical instrument 12, may be used. For example, a switch designed to be worn by a surgeon, for example on a surgeon's thumb, may be used to activate and/or deactivate the electrosurgical instrument 12. A switch may be incorporated into a cuff or strap that is placed on or around the thumb or finger of a surgeon. Alternatively, a switch may be designed to fit comfortably in a surgeon's palm.

One or more visual and/or audible signals used to alert a surgeon to the completion or resumption of ablation, conductive fluid delivery and/or power delivery, for example, may be incorporated into the electrosurgical instrument 12. For example, a beeping tone or flashing light that increases in frequency as the ablation period ends or begins may be used. Alternatively or in addition, an indicator light otherwise located on the electrosurgical instrument can be inductively coupled to the power source 16 and adapted such that when power is being delivered to the electrosurgical instrument 12, the light is visible to the surgeon or other users.

Figure 8A:
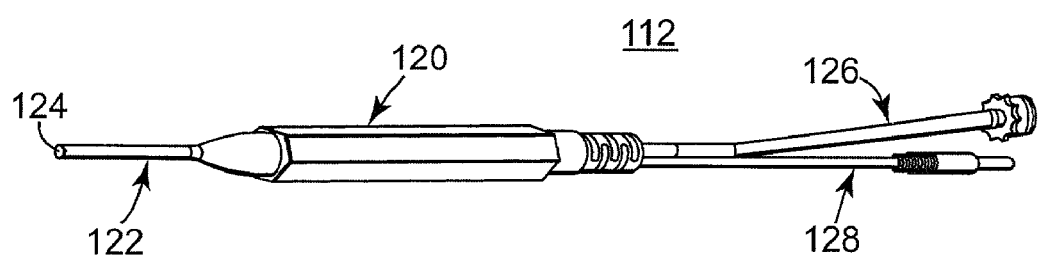
FIGS. 8A and 8B are side perspective views of an alternative electrosurgical instrument in accordance with the present invention.
Figure 8B:
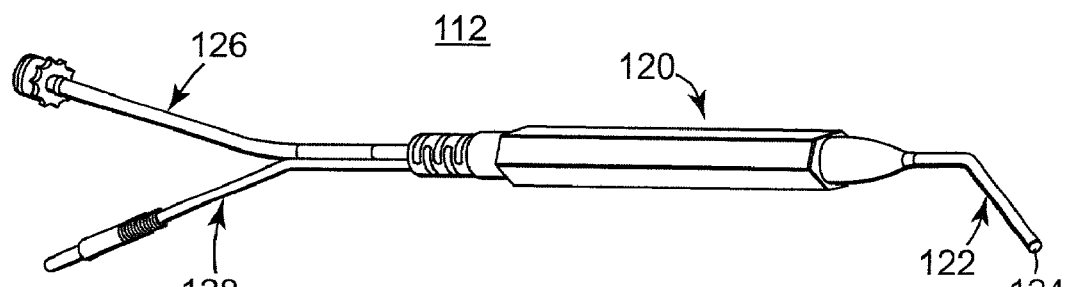

An alternative embodiment electrosurgical instrument 112 is provided in FIGS. 8A and 8D. The electrosurgical instrument 112 is highly similar to the electrosurgical instrument 12 (FIG. 1) previously described, and includes a handle 120, a shaft 122, a fluid supply tube 126 and wiring 128. The shaft 122 is virtually identical to the shaft 22 (FIG. 1) previously described, and forms a tip 124 having passages (not shown) fluidly connected to an internal lumen (not shown). Further, the shaft 122 is adapted to be bendable from a straight state (FIG. 8A) to multiple bent states (one of which is illustrated in FIG. 8B), with the shaft 122 independently maintaining a shape associated with the particular state. Similar to previous embodiments, the fluid supply tube 126 fluidly connects the fluid source 14 (FIG. 1) to the shaft 122, whereas the wiring 128 electrically connects the power source 16 (FIG. 1) to the shaft 122.

The handle 120 varies from the handle 20 (FIG. 1) previously described in that the handle 120 does not define a curved outer surface. Instead, the handle 120 is hexagonal in transverse cross-section. This alternative configuration is, however, indifferent to rotational orientation when grasped by a user, thereby promoting the preferred ease of use feature previously described. Notably, the handle 120 can alternatively be formed to a variety of other symmetrical transverse cross-sectional shapes (e.g., octagonal, etc.).

In yet another alternative embodiment, the electrosurgical system 10 (FIG. 1) further includes a controller (not shown) that can also gather and process information from the electrosurgical instrument 12, 120, fluid source 14 and/or one or more sensors or sensing elements such as temperature sensors or probes. The information supplied to or gathered by the controller can be used to adjust, for example, conductive fluid delivery, power levels, and/or energization times. For example, a temperature sensor coupled to the controller can be located in the distal section 42 (FIG. 1) of the electrosurgical instrument 12. The temperature sensor can be a thermocouple element that measures the temperature of the tip 44 rather than the temperature of the conductive fluid or the temperature of the tissue being ablated. Alternatively, the temperature sensor can be a thermocouple element that measures the temperature of the conductive fluid or a thermocouple element that measures the temperature of the tissue being ablated. When the ablation site is being irrigated with a conductive fluid, the temperature of the tissue may differ to some degree from the temperature of the conductive fluid or the temperature of the tip 44.

Heat, 1.0 kcal/g, is required to raise the temperature of water, present at the ablation site, by 1° C. However, due to the unique chemical structure of the water molecule, additional heat is required for water to change phase from the liquid phase to the gaseous phase. If the temperature at the ablation site exceeds 100° C., water will change phase, boil and may result in an audible "steam pop" within the tissue. This pop may damage and even rupture the tissue. Therefore, it is desirable to prevent the ablation site from getting to hot. In addition, to form a permanent ablation lesion the temperature of the tissue at the ablation site must be elevated to approximately 50° C. or greater. For these reasons, it is desirable to use one or more temperature-sensing elements such as, for example, thermocouples, thermistors, temperature-sensing liquid crystals, temperature-sensing chemicals, thermal cameras, and/or infrared (IR) fiber optics, to monitor the temperature of the ablation site during the ablation procedure.

Figure 9A:
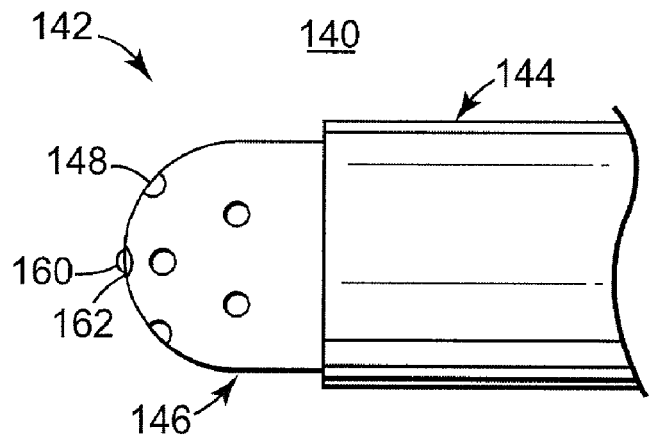
FIG. 9A is an enlarged, perspective view of a distal portion of an alternative embodiment electrosurgical instrument in accordance with the present invention.
Figure 9B:
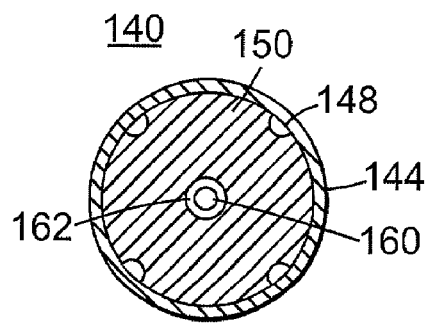
FIG. 9B is an enlarged, transverse, cross-sectional view of the electrosurgical instrument of FIG. 9A.
Figure 9C:
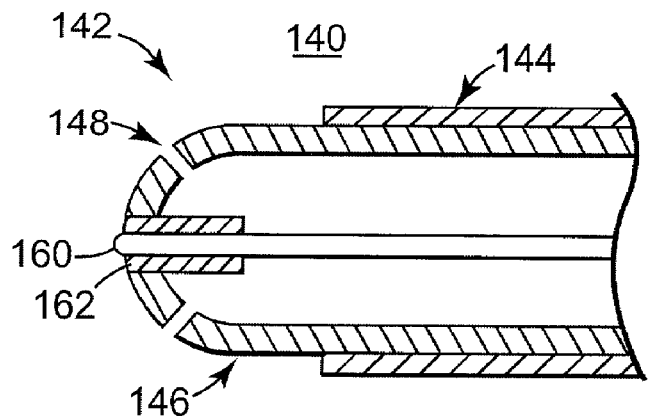
FIG. 9C is an enlarged, longitudinal, cross-sectional view of the electrosurgical instrument of FIG. 9A.

With the above in mind, FIGS. 9A-9C depict a portion of an alternative embodiment electrosurgical device 140, and in particular a distal section 142 thereof. The electrosurgical instrument 140 is highly similar to previous embodiments, and includes a shaft 144 terminating at an electrically conductive tip 146 having passages 148 formed therein that are fluidly connected to an internal lumen 150. Further, the electrosurgical instrument 140 includes a temperature probe 160 for monitoring tissue temperature of the tissue being ablated. The temperature probe 160 is placed at the tip 146. A ring of insulation material 162 may be used to electrically and thermally isolate the temperature probe 160 from the electrically conductive tip 146. The preferred central placement of the temperature probe 160 at the tip 146 allows the temperature probe 160 to directly contact a tissue surface in a number of orientations. The preferred insulating material 162 helps to prevent the thermal mass of the tip 146 and the RF energy from interfering with temperature information otherwise provided by the probe 160.

Figure 10B:
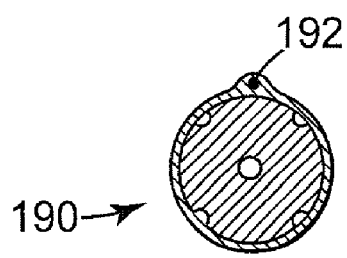
FIG. 10B is an enlarged, cross-sectional view of the electrosurgical instrument of FIG. 10A.
Figure 10A:
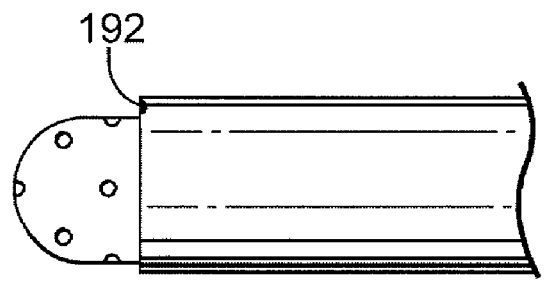
FIG. 10A is an enlarged, perspective view of a distal portion of an alternative embodiment electrosurgical instrument in accordance with the present invention.
Figure 10D:
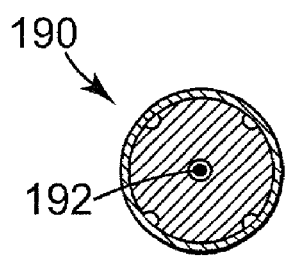
FIG. 10D is an enlarged, cross-sectional view of a portion of the electrosurgical instrument of FIG. 10C.
Figure 10C:
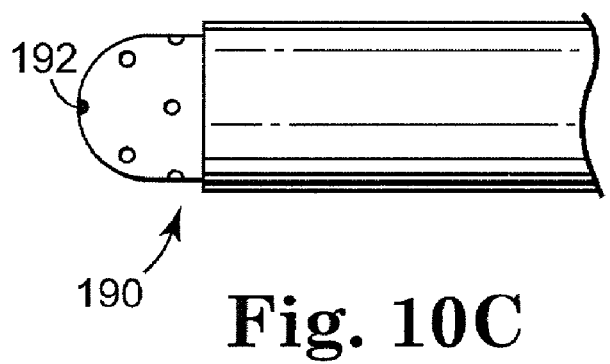
FIG. 10C is an enlarged, perspective view of a distal portion of an alternative embodiment electrosurgical instrument in accordance with the present invention.

An alternative embodiment for monitoring temperature includes an IR optical fiber system. As shown in FIGS. 10A-10D, an alternative embodiment electrosurgical instrument 190 may include an optical fiber 192 for monitoring temperature based on IR. The optical fiber 192 can be positioned adjacent a tip 194 otherwise defined by the instrument 190 (FIGS. 10A and 10B) or within the tip 194 itself (FIGS. 10C and 10D).

The above-described temperature-sensing elements 160, 192 can be used to adjust, for example, conductive fluid delivery, power levels, and/or ablation times. Temperature-sensing elements can be coupled to a visual and/or audible signal used to alert a surgeon to a variety of thermal conditions. For example, a beeping tone or flashing light that increases in frequency as temperature of the tissue, the conductive fluid and/or electrosurgical instrument is increased and/or as temperature exceeds a predetermined amount can be used.

Along these same lines, the above-mentioned controller can incorporate one or more switches to facilitate regulation of the various components of the electrosurgical system 10 (FIG. 1) by the surgeon. One example of such a switch is a foot pedal. The switch can also be, for example, a hand switch as described above, or a voice-activated switch comprising voice-recognition technologies. The switch can be incorporated in or on one of the surgeon's instruments, such as surgical site retractor, e.g., a sternal or rib retractor, or the electrosurgical instrument 12 (FIG. 1), or any other location easily and quickly accessed by the surgeon. The controller can also include a display or other means of indicating the status of various components to the surgeon, such as a numerical display, gauges, a monitor display or audio feedback.

Finally, a visual and/or audible signal used to alert a surgeon to the completion or resumption of ablation, sensing, monitoring, and/or delivery of conductive fluid can be incorporated into the controller. For example, a beeping tone or flashing light that increases in frequency as the ablation or electrocautery period ends or begins can be provided.

In yet another alternative embodiment, the fluid source 14 can be slaved to the electrosurgical instrument 12, the power source 16 and/or one or more sensors (as previously described). For example, the fluid source 14 can be designed to automatically stop or start the delivery of conductive fluid during the delivery of RF energy. Conversely, the delivery of RF energy may be slaved to the delivery of conductive fluid. That is the delivery of RF energy to the tip 44 would be coupled to the delivery of conductive fluid to the tip 44. If the flow of conductive fluid to the tip 44 were stopped, the RF energy delivered to the tip 44 would also automatically stop. For example, a switch responsive to the delivery of conductive fluid to the tip 44 for controlling RF energy delivery to the tip 44 can be incorporated into the electrosurgical instrument 12. The switch can be located, for example, within the shaft 22 or the handle 20 of electrosurgical instrument 12.

Figure 11:
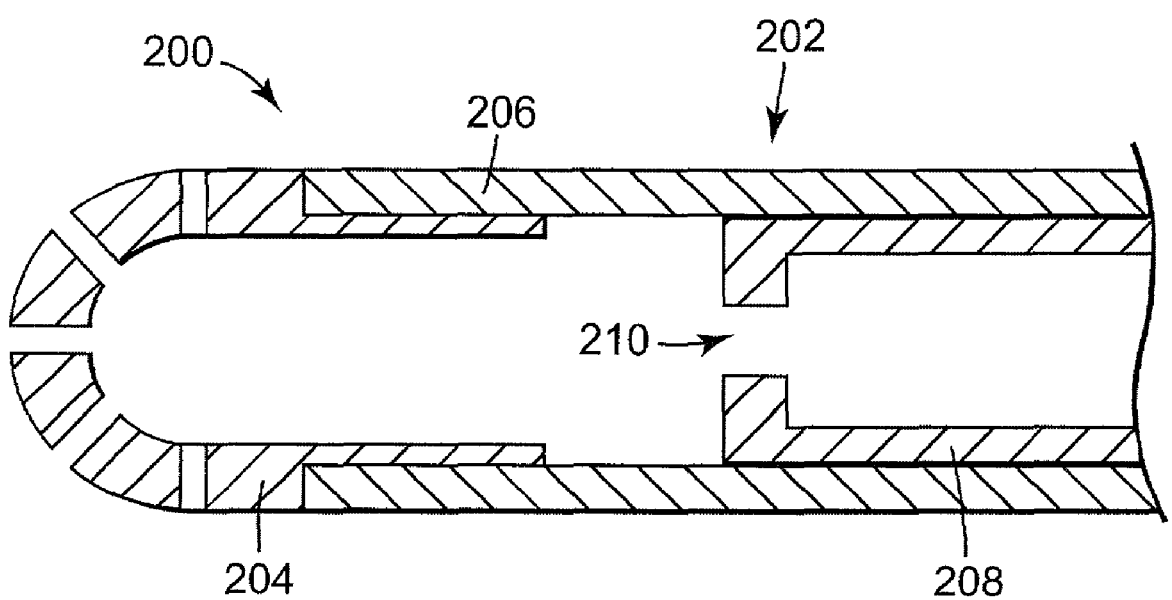
FIG. 11 is an enlarged, cross-sectional view of a portion of an alternative embodiment electrosurgical instrument in accordance with the present invention.
Figure 12:
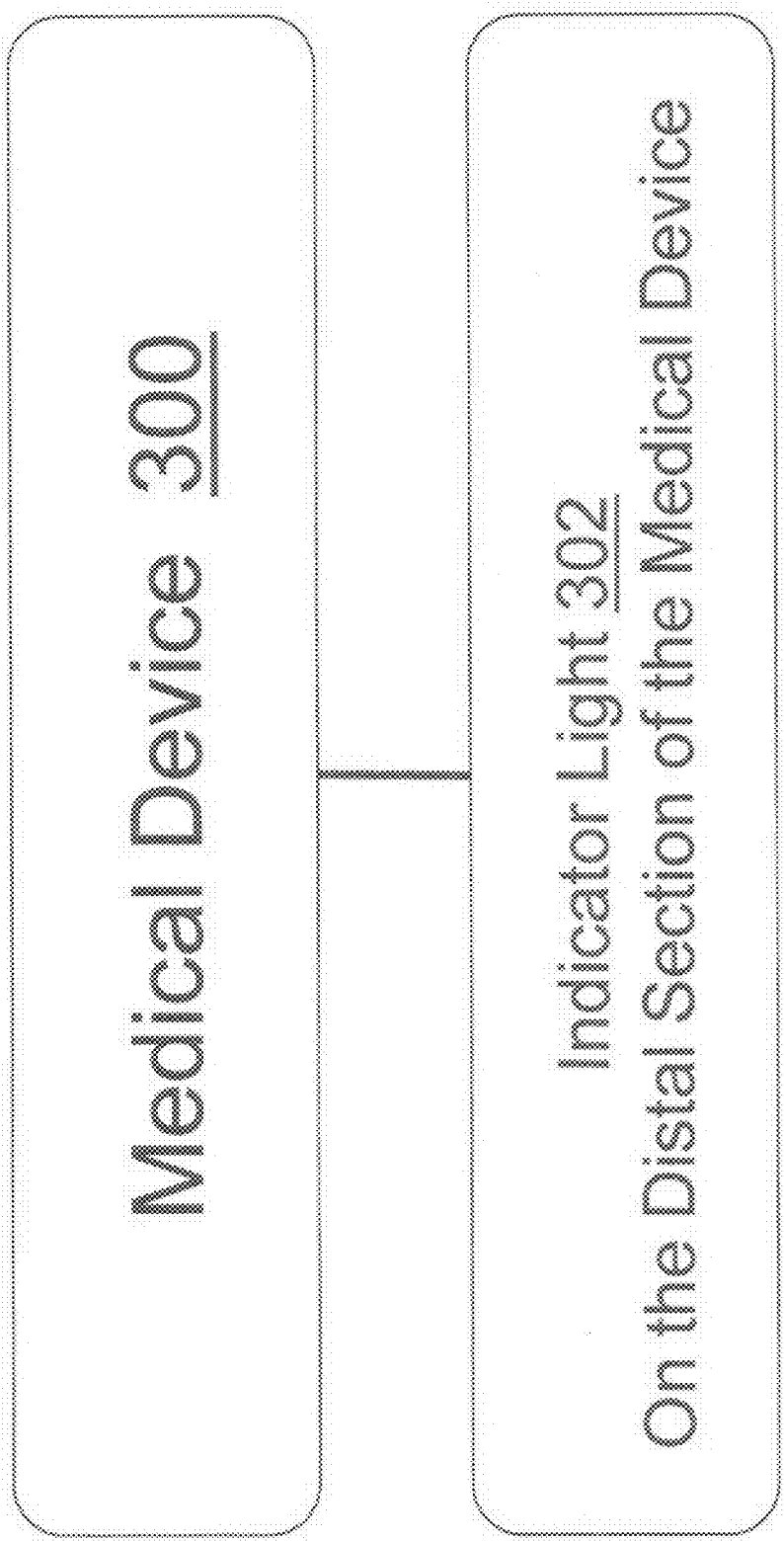
FIG. 12 is a schematic illustration of a medical device 300 and an indicator light 302 on the medical device.

With the above in mind, FIG. 11 illustrates a portion of an alternative embodiment electrosurgical instrument 200 including a shaft 202 extending from a handle (not shown). The shaft 202 includes an electrically conductive tip 204 and a malleable, non-conductive tube 206 rigidly connecting the tip 204 to the handle. An electrically conducting switch piston 208 is located within the non-conductive tube 206. The conducting switch piston 208 is electrically coupled to the power source 16 (FIG. 1). The conducting switch piston 208 is movably held in a non-contacting position relative to the tip 204 by a spring or other elastic means (not shown). As conductive fluid is delivered, a pressure develops behind an orifice 210 of the conducting switch piston 208. The size and shape of the orifice 210 is selected based on expected fluid delivery rates and pressures. When the necessary pressure or force to over come the spring retaining pressure or force is reached, the conducting switch 208 travels distally towards the tip 204, thereby making an electrical contact with the tip 204. Other means can be used to slave the delivery of power to the tip 204 of the electrosurgical instrument 200 to the delivery of conductive fluid to the tip 204 of the electrosurgical instrument 200. For example, the controller can incorporate one or more switches to facilitate the regulation of RF energy based on the delivery of conductive fluid.

In yet another embodiment, and with general reference to FIG. 1, the electrosurgical instrument 12, the fluid source 14 and/or the power source 16 can be slaved to a robotic system or a robotic system may be slaved to the electrosurgical instrument 12, the fluid source 14 and/or the power source 16.

The electrosurgical system, and in particular the electrosurgical instrument, of the present invention provides a marked improvement over previous designs. The handle and shaft are configured to be indifferent to rotational orientation when initially presented to a surgeon. Subsequently, the surgeon can conveniently shape or bend the shaft so as to provide a shape most conducive to forming the lesion pattern required by the particular surgical procedure. In this regard, the shaft independently maintains the selected shape throughout the particular electrosurgical procedure. Subsequently, the shaft can be re-shaped back to a straight configuration, or to any other desired curvature.

Although the invention has been described above in connection with particular embodiments and examples, it will be appreciated by those skilled in the art that the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

What is claimed is:

1. A medical device for use in a medical procedure comprising:
    a manually graspable handle;
    an elongated shaft projecting from the handle, the shaft being sized and shaped to be positioned through a small incision in the chest of a patient and defining a proximal section comprising a rigid, elongated metal tube and a distal section comprising metal and a rounded distal tip portion adapted to be slid relative to tissue, the shaft including a joint comprising a pin that moveably couples the distal section to the proximal section thereby allowing the distal section to pivot relative to the proximal section;
    a non-conductive material surrounding at least a portion of the elongated shaft;
    a remote actuator proximal the distal section for selectively controlling the actuation of the joint;
    a power source comprising a battery;
    a light located on the distal section and electrically coupled to the power source; and
    a switch located on the medical device for activating the delivery of electrical power from the power source, wherein the light is visible when power is being delivered.

2. The medical device of claim 1, wherein the distal section includes a passage.

3. The medical device of claim 1, wherein the distal section includes an opening.

4. The medical device of claim 1, wherein the distal section includes a hole.

5. The medical device of claim 1, wherein the distal section includes a slot.

6. The medical device of claim 1, wherein the actuator comprises a knob.

7. The medical device of claim 1, wherein the actuator comprises a button.

8. The medical device of claim 1, wherein the actuator comprises a lever.

9. The medical device of claim 1, wherein the actuator comprises a slide.

10. The medical device of claim 1, wherein at least a portion of the distal section of the elongated shaft defines a uniform radius of curvature.

11. The medical device of claim 1, wherein the handle is rigidly coupled to the shaft such that the shaft is readily manipulated via movement of the handle.

12. The medical device of claim 1, further comprising a sensor located at the distal section of the elongated shaft.

13. The medical device of claim 1, wherein the actuator is located at the handle.

14. The medical device of claim 1, wherein the proximal section includes an internal lumen.

15. The medical device of claim 1, wherein at least a portion of the shaft is malleable.

16. The medical device of claim 1, wherein the medical procedure is an ablation procedure.

17. A medical device for use in a medical procedure comprising:
    a manually graspable, non-conductive handle;
    an elongated shaft projecting from the handle, the shaft being sized and shaped to be positioned through a small incision in the chest of a patient and defining a proximal section comprising a rigid, elongated metal tube and a distal section comprising metal and a rounded tip portion adapted to be slid relative to tissue, the rounded tip portion being free of any electrode movable relative to the rounded tip portion, the shaft including a joint comprising a pin that moveably couples the distal section to the proximal section thereby allowing the distal section to pivot relative to the proximal section;
    a non-conductive material surrounding at least a portion of the elongated shaft;
    a remote actuator located at the handle for selectively controlling the actuation of the joint;
    a power source comprising a battery;
    a light located on the medical device and electrically coupled to the power source; and
    an activator located at the handle for activating the delivery of power from the power source, wherein the light is visible when power is being delivered.

* * * * *